(12) United States Patent
Cowens et al.

(10) Patent No.: US 11,806,029 B2
(45) Date of Patent: Nov. 7, 2023

(54) LOCKING TROCAR AND METHOD OF USING THE SAME

(71) Applicant: DEPUY SYNTHES PRODUCTS, INC., Raynham, MA (US)

(72) Inventors: David Cowens, West Chester, PA (US); Mark Thibeault, Brookline, NH (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 179 days.

(21) Appl. No.: 17/142,374

(22) Filed: Jan. 6, 2021

(65) Prior Publication Data
US 2022/0211394 A1 Jul. 7, 2022

(51) Int. Cl.
*A61B 17/17* (2006.01)
*A61B 17/34* (2006.01)

(52) U.S. Cl.
CPC ...... *A61B 17/1717* (2013.01); *A61B 17/1728* (2013.01); *A61B 17/3468* (2013.01); *A61B 17/3472* (2013.01); *A61B 2017/347* (2013.01)

(58) Field of Classification Search
CPC ............ A61B 17/1717; A61B 17/1778; A61B 17/3468; A61B 17/3472
See application file for complete search history.

(56) References Cited

U.S. PATENT DOCUMENTS

| 4,398,322 | A | 8/1983 | Ewen |
|---|---|---|---|
| 5,122,146 | A | 6/1992 | Chapman et al. |
| 5,207,682 | A | 5/1993 | Cripe |
| 5,458,602 | A | 10/1995 | Goble et al. |
| 5,620,456 | A | 4/1997 | Sauer et al. |
| 5,704,941 | A | 1/1998 | Jacober et al. |
| 6,126,359 | A | 10/2000 | Dittrich et al. |
| 6,258,095 | B1 | 7/2001 | Lombardo et al. |
| 6,783,529 | B2 | 8/2004 | Hover et al. |

(Continued)

FOREIGN PATENT DOCUMENTS

| CN | 203619652 A1 | 6/2014 |
|---|---|---|
| CN | 203935262 U | 11/2014 |

(Continued)

OTHER PUBLICATIONS

Invitation Pay Additional Fees with Partial International Search Results, PCT/IB2021/062032; 13 pages.

(Continued)

*Primary Examiner* — Sameh R Boles

(57) ABSTRACT

An aiming arm system comprises an aiming arm and a guide sleeve. The aiming arm has 1) a body and a guide hole that extends through the body along a hole axis, and 2) a retention element supported relative to the body. The aiming arm is configured to be positioned such that the hole axis is aligned with a target location of an anatomical implant. The guide sleeve extends along a linear direction, and is sized to be inserted through the guide hole in the linear direction. Relative rotation between the guide sleeve and the retention element transitions the aiming arm system between an unlocked configuration whereby the guide sleeve is insertable through the guide hole, and a locked configuration whereby the retention element applies a retention force to the guide sleeve that substantially prevents the guide sleeve from moving further along the linear direction.

3 Claims, 18 Drawing Sheets

(56) References Cited

U.S. PATENT DOCUMENTS

| | | |
|---|---|---|
| 7,077,847 B2 | 7/2006 | Pusnik et al. |
| 7,131,974 B2 | 11/2006 | Keyer et al. |
| 7,311,710 B2 | 12/2007 | Zander |
| 7,357,804 B2 | 4/2008 | Binder, Jr. et al. |
| 7,549,994 B2 | 6/2009 | Zander et al. |
| 7,618,420 B2 | 11/2009 | Collazo |
| 7,621,921 B2 | 11/2009 | Parker |
| 8,080,015 B2 | 12/2011 | Buttler et al. |
| 8,337,533 B2 | 12/2012 | Raines et al. |
| 8,361,077 B2 | 1/2013 | Keller |
| 8,486,072 B2 | 7/2013 | Haininger |
| 8,668,694 B2 | 3/2014 | Teeny |
| 8,753,343 B2 | 6/2014 | Staeubli |
| 8,764,752 B2 | 7/2014 | Buettler et al. |
| 9,066,764 B2 | 6/2015 | Perez |
| 9,308,004 B2 | 4/2016 | Giersch et al. |
| 9,393,064 B2 | 7/2016 | Roethlisberger et al. |
| 9,439,780 B2 | 9/2016 | Witt et al. |
| 9,463,053 B2 | 10/2016 | Garino |
| 9,463,054 B2 | 10/2016 | Mueckter |
| 9,968,389 B2 | 5/2018 | Garino |
| 9,993,267 B2 | 6/2018 | Orsak et al. |
| 10,206,724 B2 | 2/2019 | Williams |
| 10,258,402 B2 | 4/2019 | Silva et al. |
| 10,327,824 B2 | 6/2019 | Ricker et al. |
| 2003/0135211 A1 | 7/2003 | Cho |
| 2003/0135212 A1 | 7/2003 | Chow |
| 2009/0177240 A1 | 7/2009 | Perez |
| 2011/0245885 A1* | 10/2011 | Powell ............... A61B 17/1725 606/86 R |
| 2014/0094821 A1 | 4/2014 | Wagner et al. |
| 2014/0214101 A1 | 7/2014 | Roethlisberger et al. |
| 2016/0175112 A1 | 6/2016 | Pruvost et al. |
| 2017/0056081 A1 | 3/2017 | Langdale et al. |
| 2019/0133651 A1 | 5/2019 | Williams |
| 2019/0262046 A1 | 8/2019 | Ricker et al. |

FOREIGN PATENT DOCUMENTS

| | | |
|---|---|---|
| DE | 20211806 U1 | 10/2002 |
| EP | 1398000 B1 | 8/2006 |
| EP | 1398001 B1 | 8/2008 |
| EP | 2030596 A1 | 3/2009 |
| EP | 2349039 B1 | 9/2009 |
| EP | 3122290 B1 | 8/2019 |
| IN | 201003084 A | 11/2010 |
| WO | 2011017066 A1 | 2/2011 |
| WO | 2011/046784 A1 | 4/2011 |
| WO | 2015144772 A1 | 10/2015 |
| WO | 2017198748 A1 | 11/2017 |
| WO | 2018072181 A1 | 4/2018 |

OTHER PUBLICATIONS

International Search Report and The Written Opinion of the International Searching Authority, PCT/IB2021/062032, 8 pages.

Interprosthetic and Peri-Implant Fractures: Principles of Operative Fixation and Future Directions, By Liporace et al., J Orthop Trauma, vol. 31, No. 5, May 2017, pp. 287-292. (www.jorthotrauma.com).

Intramedullary Nail and Plate Combination Fixation for Complex Distal Tibia Fractures: When and How? By Yoon et al., J Orthop Trauma, vol. 30, No. 11 Supplement, Nov. 2016 pp. S17-S21 (www.jorthotrauma.com).

* cited by examiner

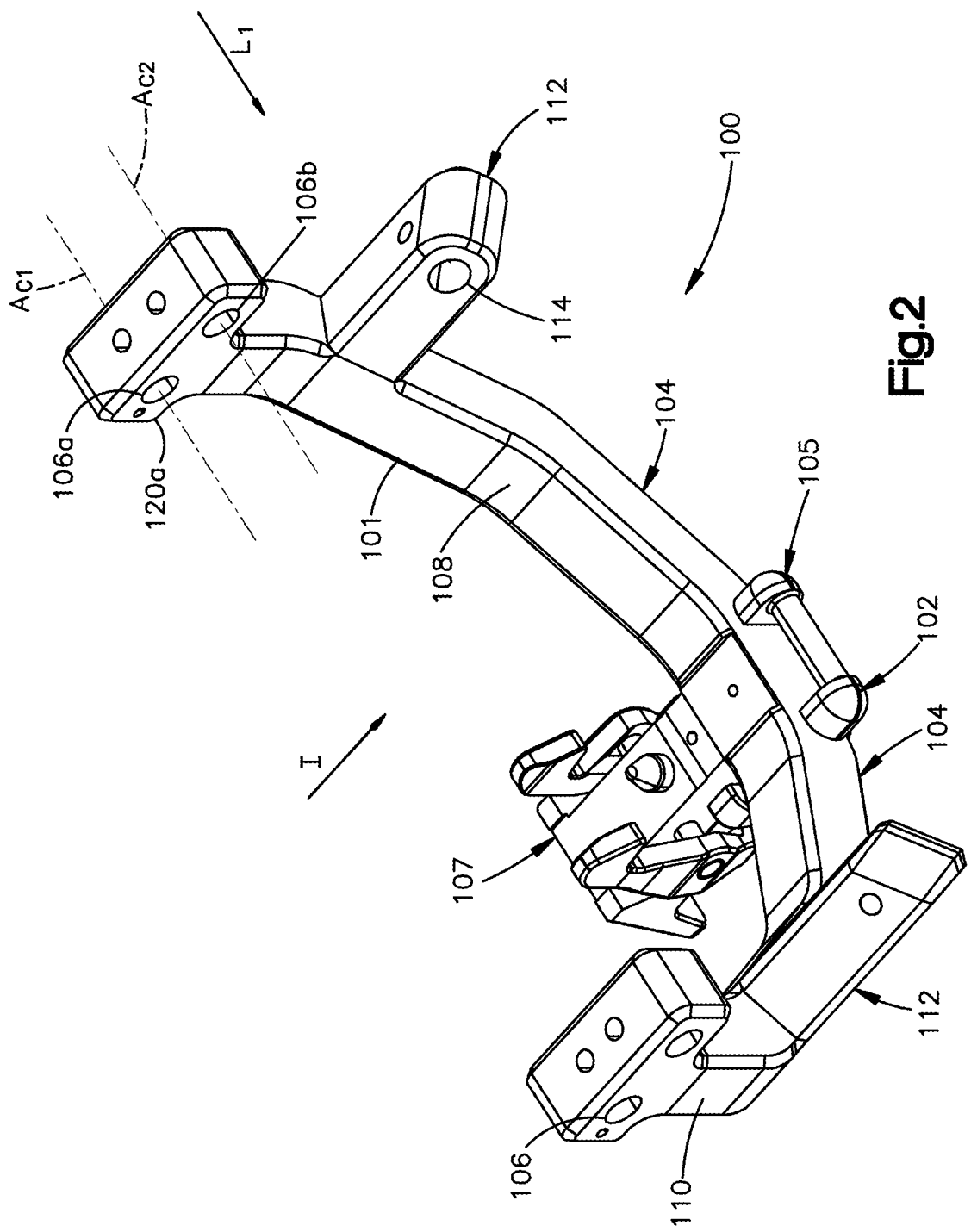

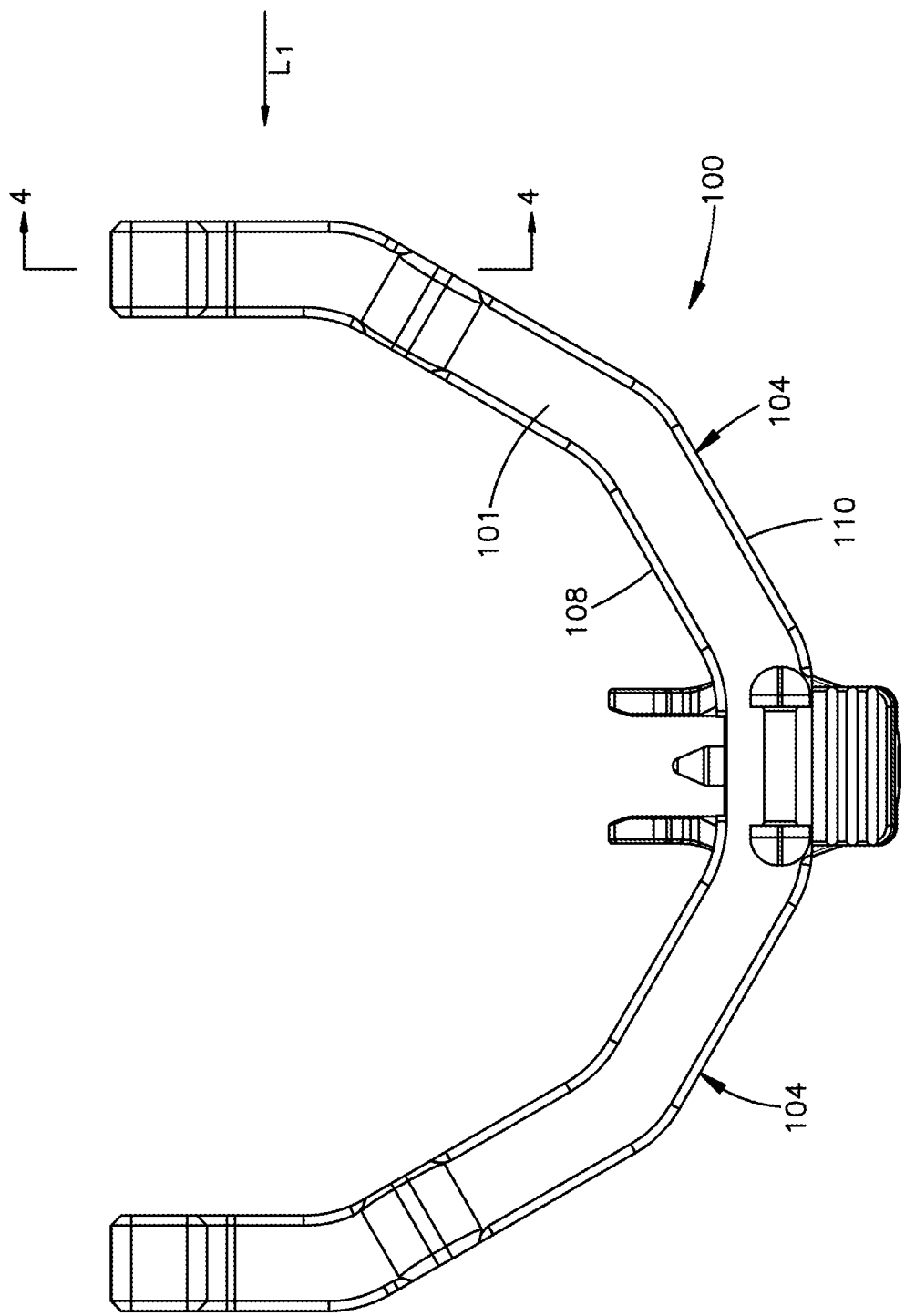

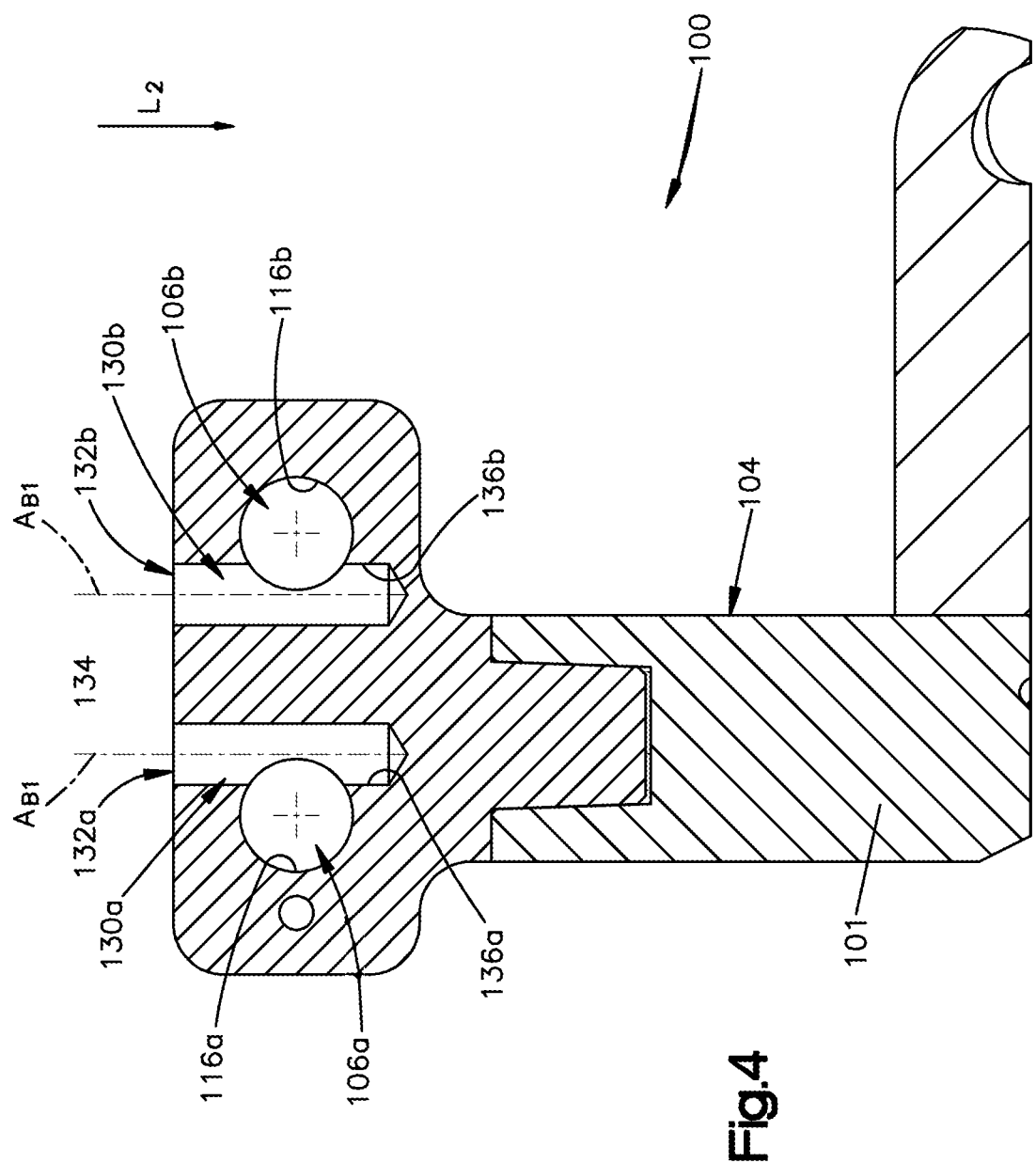

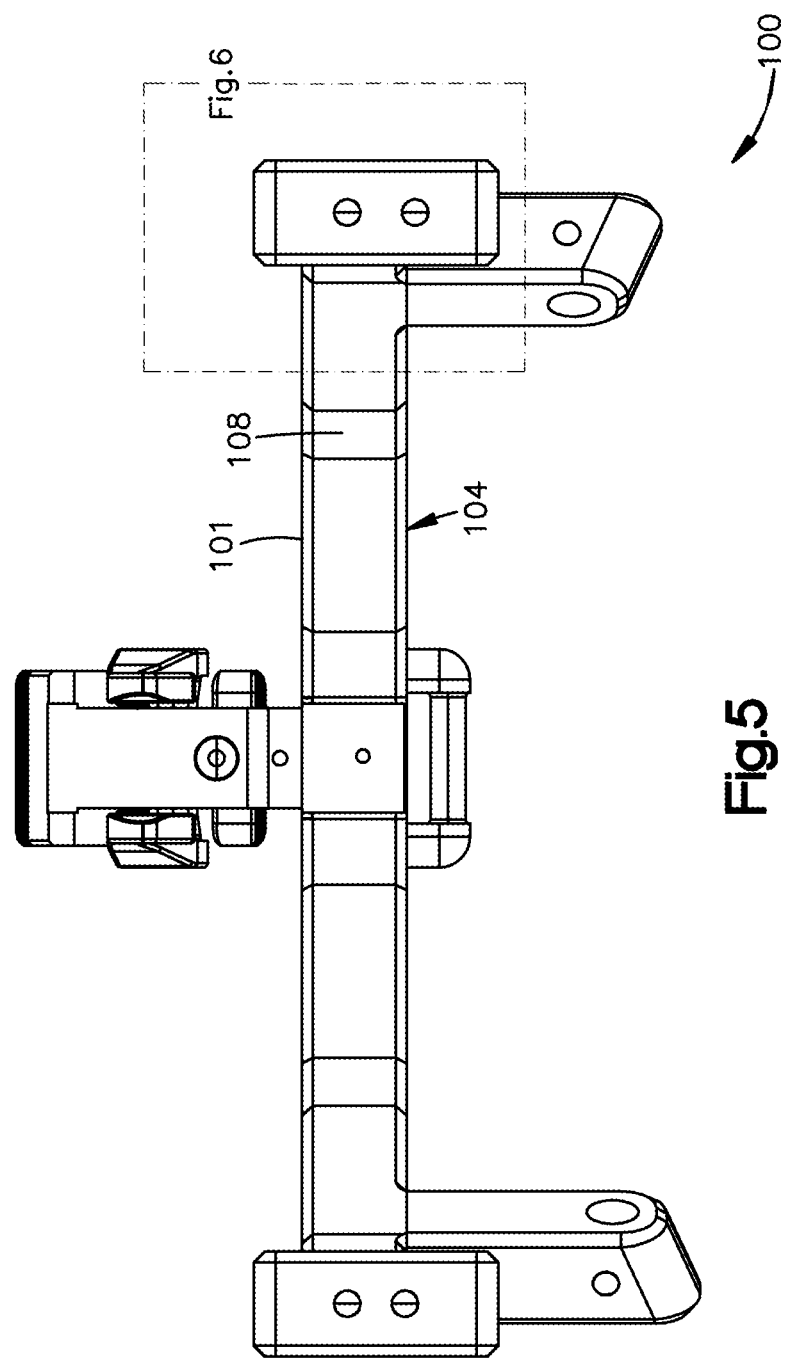

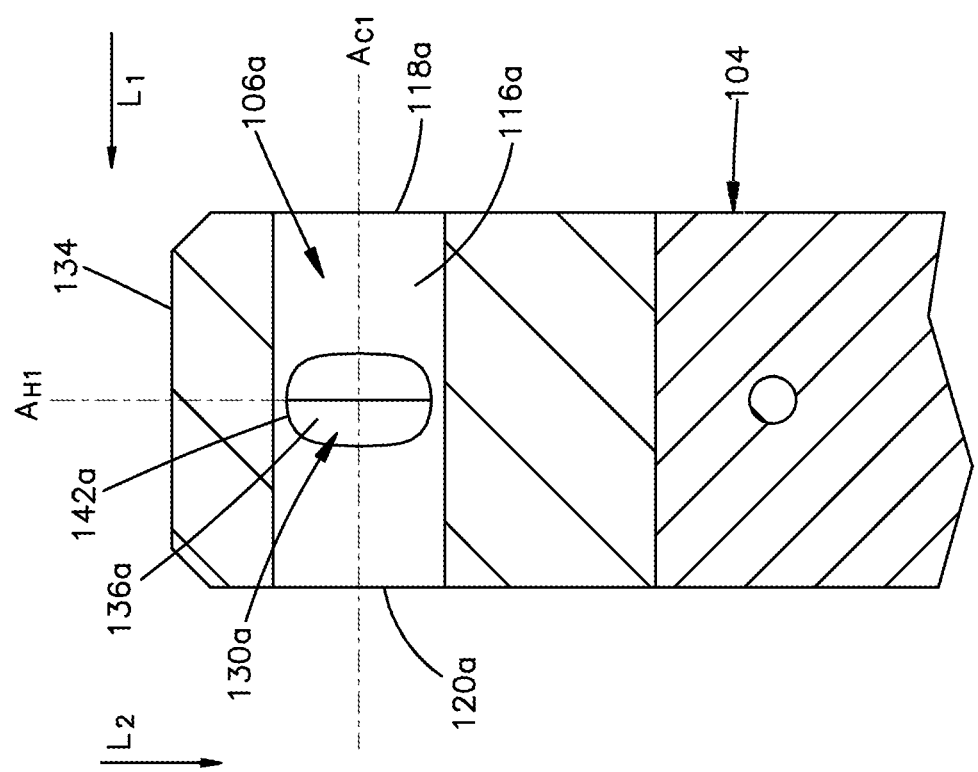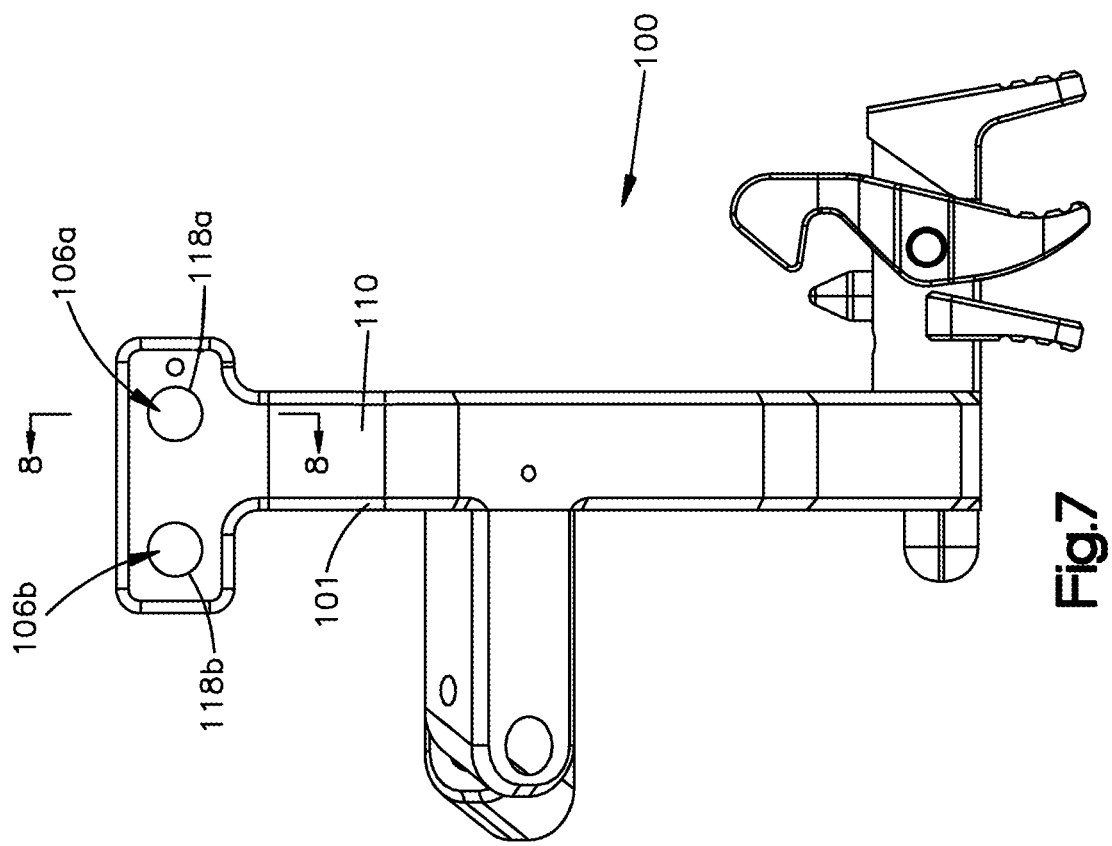

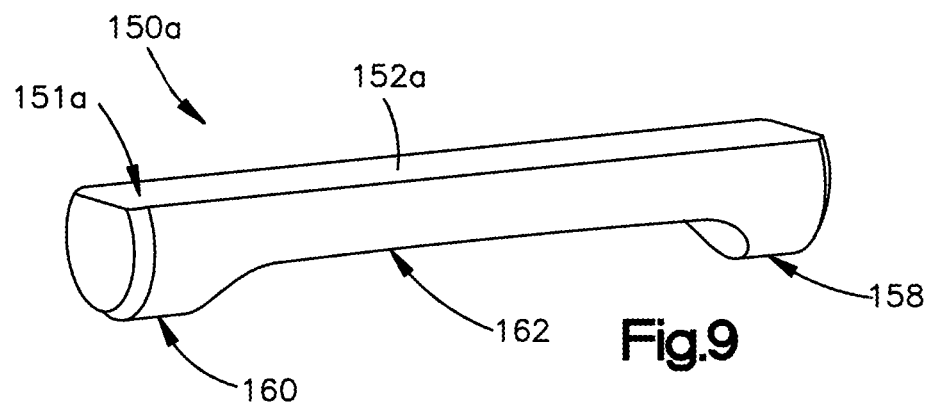
Fig.9
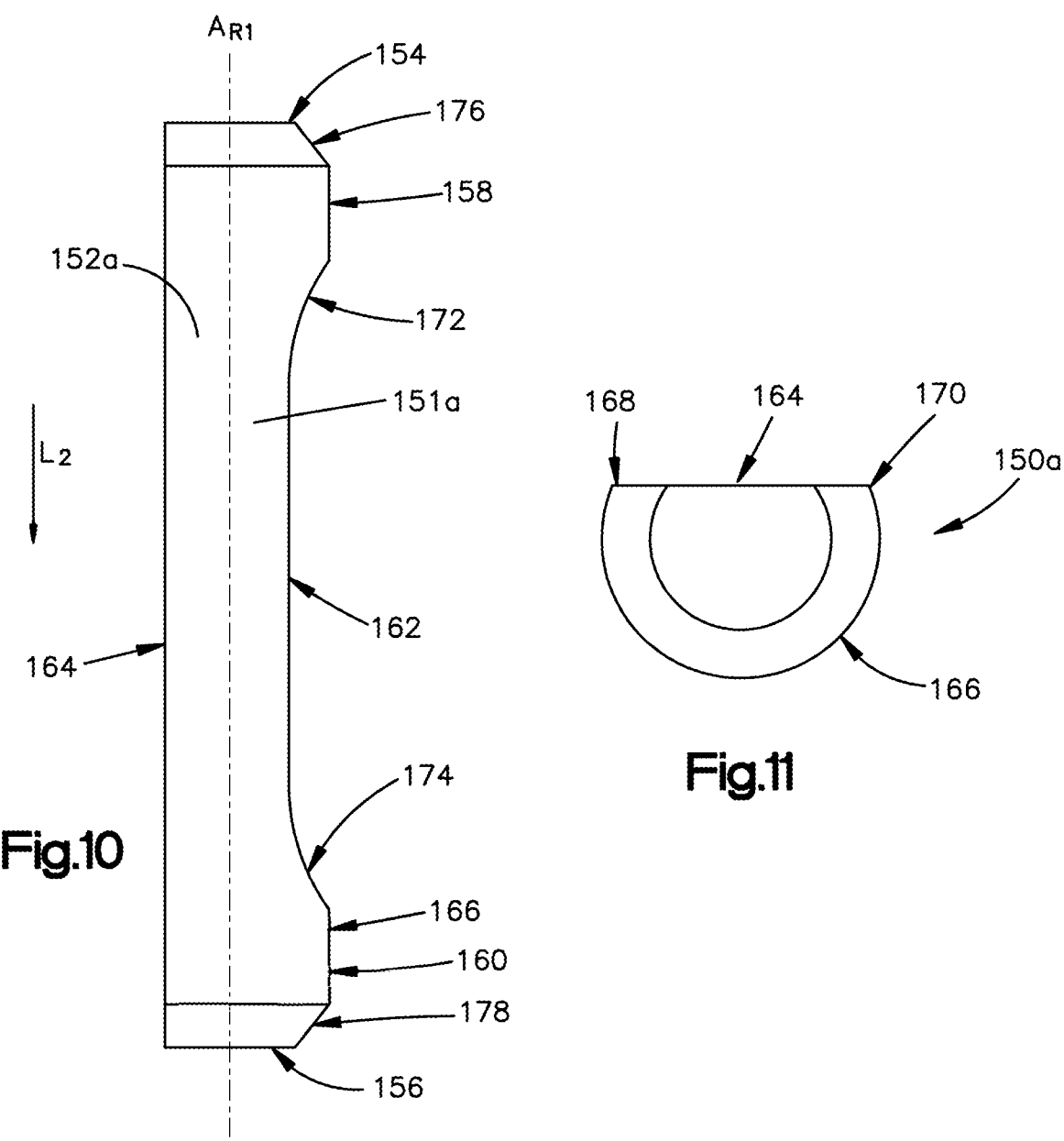
Fig.10
Fig.11

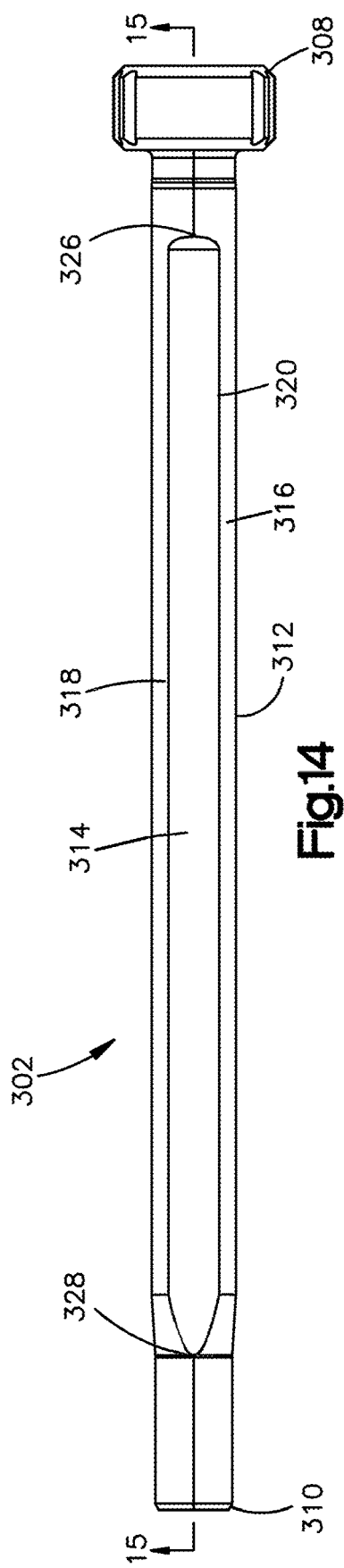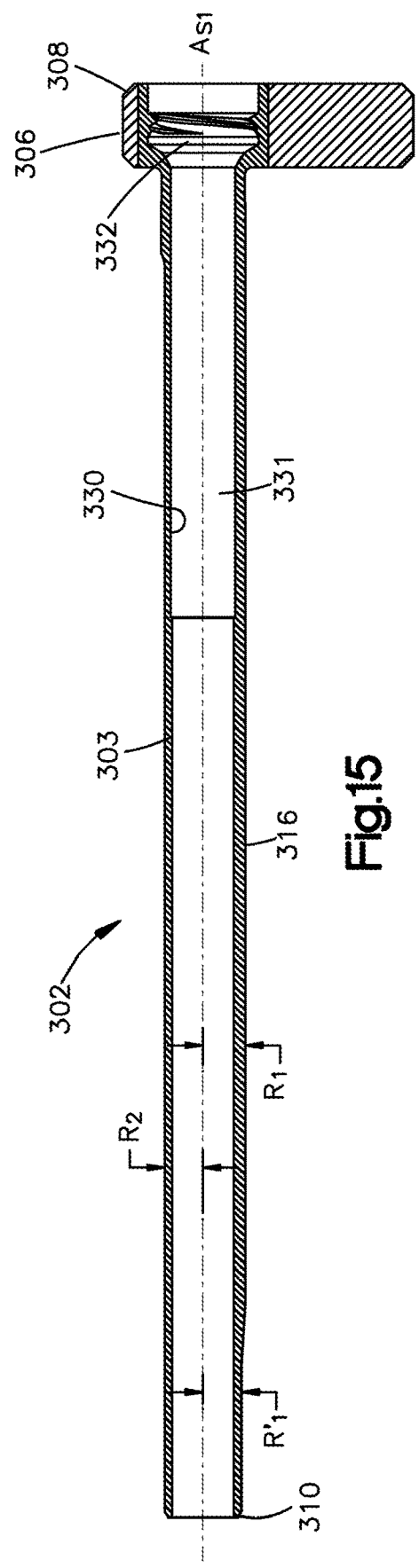

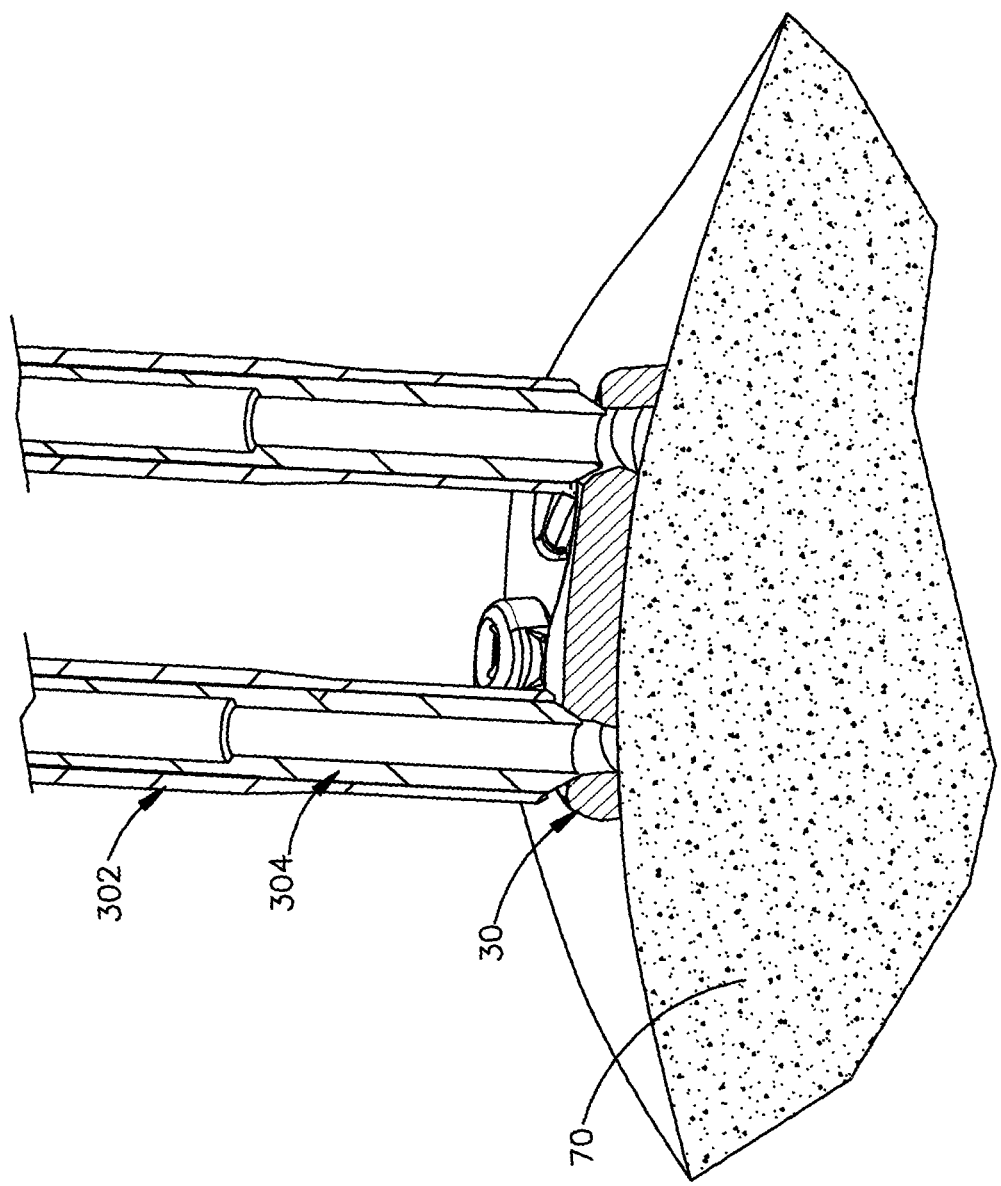

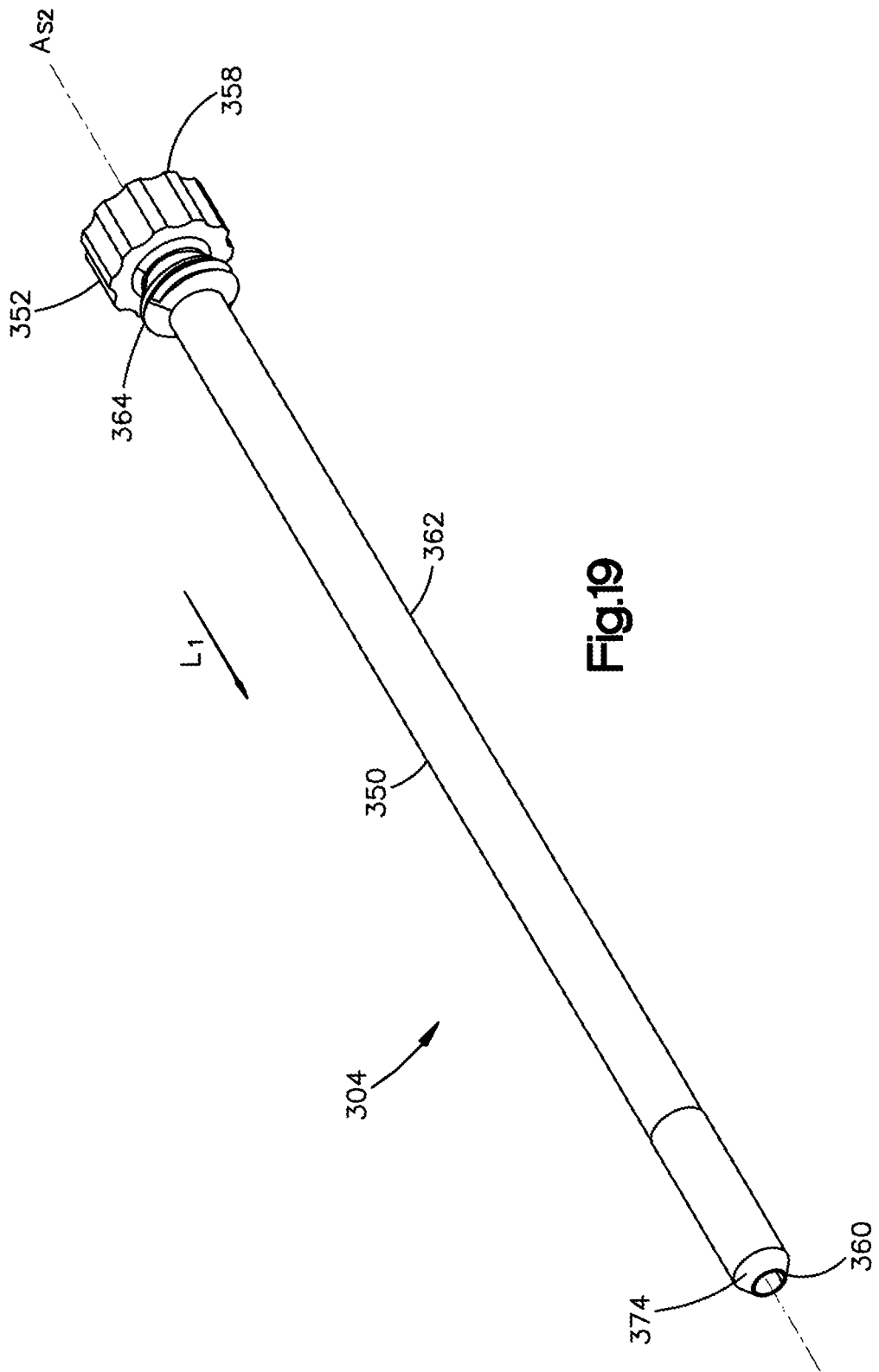

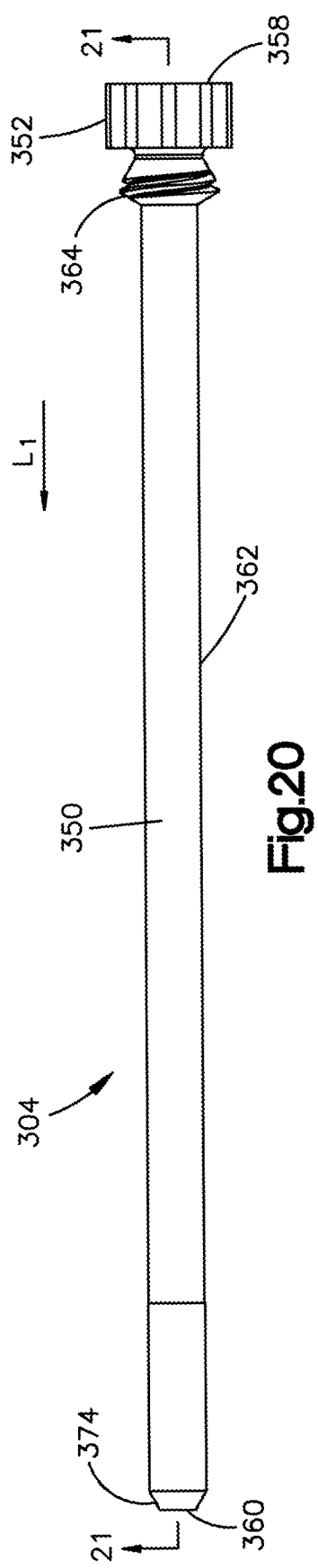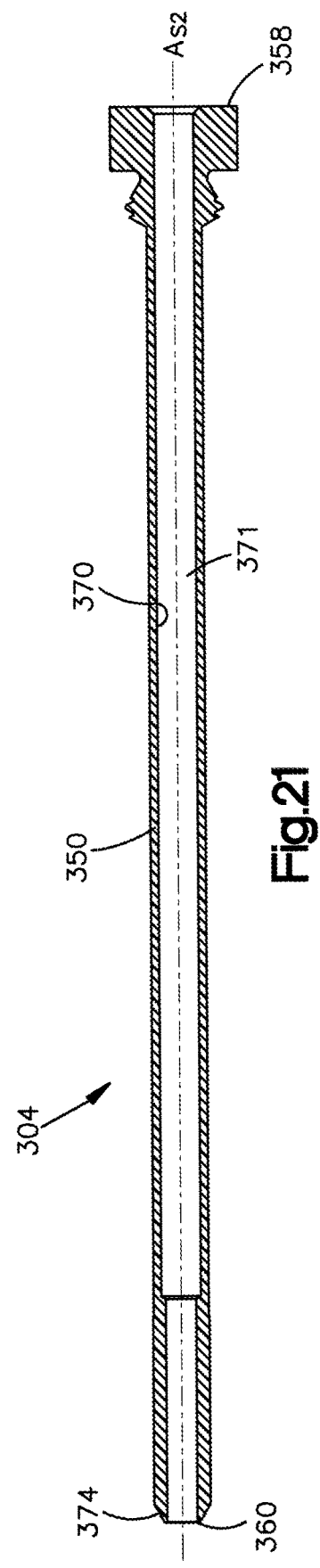

LOCKING TROCAR AND METHOD OF USING THE SAME

TECHNICAL FIELD

The present disclosure relates to systems, kits, assemblies, and methods for the alignment and attachment of an aiming guide to a bone plate for attachment to an intramedullary nail in a medullary canal of the bone.

BACKGROUND

Intramedullary nails have long been used to treat fractures in long bones of the body such as the femur, the tibia, the humerus, and the like. To treat such fractures, the intramedullary nail is inserted into a medullary canal of the long bone such that the nail extends spans across one or more fractures in the long bone to segments of the long bone that are separated by the one or more fractures. Bone anchors are then inserted through the bone and into the intramedullary nail on opposing sides of the fracture, thereby fixing the intramedullary nail to the bone. The intramedullary nail can remain in the medullary canal at least until the fracture is fused.

The foregoing background discussion is intended solely to aid the reader. It is not intended to limit the innovations described herein. Thus, the foregoing discussion should not be taken to indicate that any particular element of a prior system is unsuitable for use with the innovations described herein, nor is it intended to indicate that any element is essential in implementing the innovations described herein.

SUMMARY

In conventional intramedullary nailing techniques, a surgeon needs to lock the nail to both the distal and proximal fracture fragments after inserting the nail into the bone. To complete this technique, a series of sleeves are used to expose the target screw location, drill a pilot hole along the appropriate trajectory, and provide guidance to insert the screw through the nail. The sleeves can also be used to apply pressure to the bone as a reduction force or to temporarily hold other hardware. Current methods for this technique may be adequate for drilling and inserting a screw, but lack the ability to quickly and reliably apply and release pressure.

The foregoing needs are met, to a great extent, by the system and method disclosed in the present application.

According to an aspect of the present disclosure, a guide sleeve assembly in combination with an aiming arm system is configured to apply pressure to a lateral attachment plate and/or washer (e.g. bone plate) to hold the plate to the bone during drilling and/or screwing for the nail locking elements. The guide sleeve assembly can be applied to any circumstance whereby the surgeon needs to apply lateral pressure (e.g. to the bone as a reduction force), and lock the position of the sleeve assembly relative to the plate.

The aiming arm system includes an aiming arm guide hole for directing the guide sleeve assembly. The geometry of the guide sleeve assembly can include a non-cylindrical outer profile formed by removing material from an outer diameter along a length of an outer sleeve guide. The aiming arm guide hole includes a crossing pin (e.g. retention element) which forms a chord in the guide hole profile. When the outer sleeve guide is inserted in an unlocked orientation, the cross pin passes freely along the sleeve guide. When the outer sleeve guide is rotated in the aiming arm guide hole relative to the crossing pin, the sleeve guide creates a cam mechanism between a full outer diameter of the sleeve guide and the cross pin. This forms an interference fit between the outer sleeve guide and the cross pin, that produces enough friction between the sleeve guide and pin to substantially prevent axial movement of the sleeve guide in the guide hole.

According to another aspect of the present disclosure, an aiming arm system is provided. The aiming arm system comprises an aiming arm and a guide sleeve. The aiming arm has 1) an aiming arm body and a guide hole that extends through the aiming arm body along a central guide hole axis, wherein the aiming arm is configured to be positioned such that the central guide hole axis is aligned with a target location of an anatomical implant, and 2) a retention element supported relative to the aiming arm body. The guide sleeve extends along a central guide sleeve axis that is oriented along a linear direction, and sized to be inserted through the guide hole in the linear direction. The relative rotation between the guide sleeve and the retention element transitions the aiming arm system between an unlocked configuration whereby the guide sleeve is insertable through the guide hole along the linear direction, and a locked configuration whereby the retention element applies a retention force to the guide sleeve that substantially prevents the guide sleeve from moving further along the linear direction.

According to another aspect of the present disclosure, a method for positioning a guide sleeve within a guide hole is disclosed. The method comprises: moving a guide sleeve within a guide hole defined by an aiming arm, wherein the guide hole extends through the aiming arm body along a central guide hole axis, wherein the aiming arm is configured to be positioned such that the central guide hole axis is aligned with a target location of an anatomical implant, the aiming arm supporting a retention element; inserting the guide sleeve into the guide hole in a linear direction, wherein the guide sleeve extends along a central guide sleeve axis that is oriented along the linear direction; and transitioning the aiming arm between an unlocked configuration whereby the guide sleeve is insertable through the guide hole along the linear direction, and a locked configuration whereby the retention element applies a retention force to the guide sleeve that substantially prevents the guide sleeve from moving along the linear direction. The transitioning step occurs by relative rotation between the guide sleeve and the retention element.

This summary is provided to introduce a selection of concepts in a simplified form that are further described below in the Detailed Description section. This Summary is not intended to identify key features or essential features of the claimed subject matter, nor is it intended to be used to limit the scope of the claimed subject matter. Furthermore, the claimed subject matter is not constrained to limitations that solve any or all disadvantages noted in any part of this disclosure.

BRIEF DESCRIPTION OF THE DRAWINGS

The foregoing summary, as well as the following detailed description of illustrative embodiments of the intervertebral implant of the present application, will be better understood when read in conjunction with the appended drawings. For the purposes of illustrating the expandable intervertebral implant of the present application, there is shown in the drawings illustrative embodiments. It should be understood, however, that the application is not limited to the precise arrangements and instrumentalities shown. In the drawings:

FIG. 2 illustrates a top perspective view of an aiming arm body, according to an aspect of this disclosure;

FIG. 3 illustrates a front view of the aiming arm body shown in FIG. 2;

FIG. 4 illustrates a cross-sectional view of the aiming arm body taken along line 4-4 shown in FIG. 3;

FIG. 5 illustrates a top view of the aiming arm body shown in FIG. 2;

FIG. 7 illustrates a side view of the aiming arm body shown in FIG. 2;

FIG. 8 illustrates a cross-sectional view of the aiming arm body taken along line 8-8 shown in FIG. 7;

FIG. 9 illustrates a perspective view of a retention element, according to an aspect of this disclosure;

FIG. 10 illustrates a side view of the retention element shown in FIG. 9;

FIG. 11 illustrates a top view of the retention element shown in FIG. 9;

FIG. 14 illustrates a top view of an outer guide sleeve, according to an aspect of this disclosure;

FIG. 15 illustrates a cross-sectional view of the outer guide sleeve taken along line 15-15 in FIG. 14;

FIG. 16 illustrates a view of the guide sleeve assembly supporting the bone plate shown in FIG. 12 against a bone, according to an aspect of this disclosure;

FIG. 19 illustrates a perspective view of an inner guide sleeve, according to an aspect of this disclosure;

FIG. 20 illustrates a top view of the inner guide sleeve shown in FIG. 19;

FIG. 21 illustrates a cross-sectional view of the inner guide sleeve taken along line 21-21 in FIG. 20;

DETAILED DESCRIPTION OF ILLUSTRATIVE EMBODIMENTS

Figure 1:
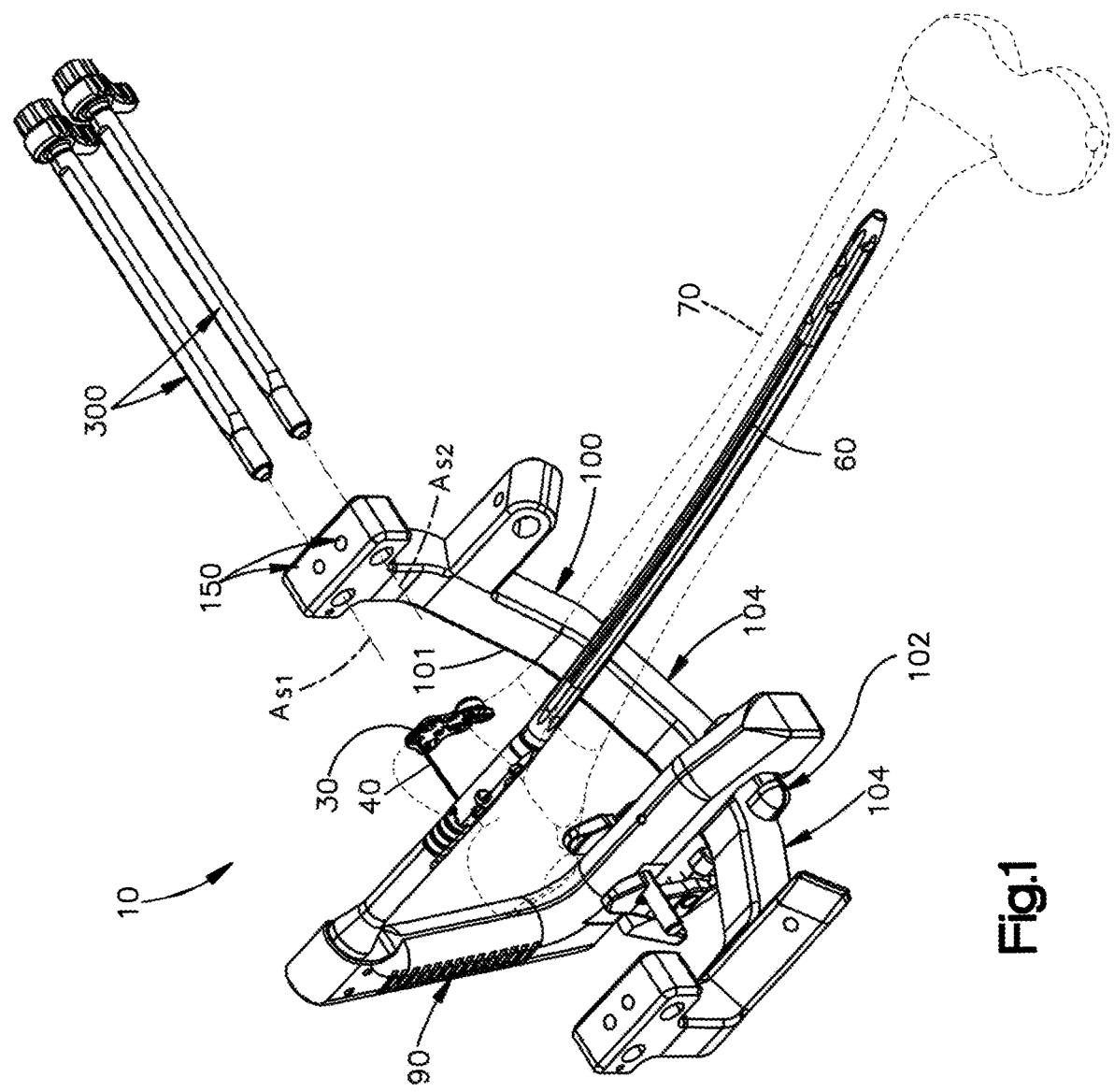
FIG. 1 illustrates a perspective view of a system according to one aspect having a guide sleeve assembly supported by an aiming arm system that is attached to an intramedullary nail received in a medullary canal of a bone.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

Certain terminology used in this description is for convenience only and is not limiting. The words "top", "bottom", "distal", "proximal", "inward", "outward", "inner", "outer", "above", "below", "axial", "transverse", "circumferential," and "radial" designate directions in the drawings to which reference is made. The words "inner", "internal", and "interior" refer to directions towards the geometric center of the implant and/or implant adjustment tools, while the words "outer", "external", and "exterior" refer to directions away from the geometric center of the implant and/or implant adjustment tools. The words, "anterior", "posterior", "superior," "inferior," "medial," "lateral," and related words and/or phrases are used to designate various positions and orientations in the human body to which reference is made. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable. The terminology includes the above-listed words, derivatives thereof and words of similar import.

As used herein, the term "substantially" and derivatives thereof, and words of similar import, when used to describe a size, shape, orientation, distance, spatial relationship, or other parameter includes the stated size, shape, orientation, distance, spatial relationship, or other parameter, and can also include a range up to 10% more and up to 10% less than the stated parameter, including 5% more and 5% less, including 3% more and 3% less, including 1% more and 1% less.

Referring to FIG. 1, a system 10 is shown that is configured to position a bone plate 30 against a surface of a bone 70 as the bone plate 30 is fastened to the bone 70 and an intramedullary nail 60. In general, the system 10 comprises an aiming arm system 100 that facilitates the alignment of the bone plate 30 with the bone 70 and the intramedullary nail 60. The aiming arm system 100 releasably attaches to a proximal end of the intramedullary nail 60 and comprises an aiming arm body 101 that has at least one aiming guide 104 (e.g. aiming arm) and a handle 90. The aiming arm system 100 can facilitate alignment of the bone plate 30 such that axes $A_{S1}$ and $A_{S2}$ of the bone plate 30 are aligned with corresponding bone-anchor apertures of the intramedullary nail 60. For example, an axis $A_{B1}$ of the bone plate 30 can be aligned with a first aperture of the bone plate 30 and a first bone-anchor opening that extends through the intramedullary nail 60, and the axis $A_{B2}$ of the bone plate 30 can be aligned with a second aperture of the bone plate 30 and a second bone-anchor opening that extends through the intramedullary nail 60.

The system 10 can further comprise at least one guide sleeve assembly 300. The aiming arm system 100 supports the guide sleeve assembly 300 so as to align the guide sleeve assembly 300 with the bone plate 30 and the intramedullary nail 60. For example, the axis $A_{B1}$ of the bone plate 30 can be aligned with a first guide sleeve assembly 300 and the axis $A_{B2}$ of the bone plate 30 can be aligned with a second guide sleeve assembly 300, as is further described below. The system 10 can further comprise at least one retention element 150 for securing each at least one guide sleeve assemblies 300 to the aiming arm system 100, as further described herein.

The system 10 can further comprise one or more of the bone plates 30, at least one bone anchor 40 such as a bone screw, the aiming arm system 100, an intramedullary nail 60, and one or more guide sleeve assemblies 300. The intramedullary nail 60 is elongate generally along a superior-inferior direction SI and is sized to be received in a medullary canal of a long bone such as a femur, tibia, or humerus.

The intramedullary nail 60 can be implanted by driving the nail 60 into a medullary canal of the bone 70. In so doing, the handle 90 can be attached to the nail 60, and a medical professional such as a surgeon can hold the handle to guide the intramedullary nail 60 into the medullary canal.

To secure the intramedullary nail 60 to the bone 70, the intramedullary nail 60 can define at least one bone-anchor fixation hole that extends at least partially through the intramedullary nail 60. For example, the intramedullary nail 60 can include at least one proximal bone-anchor fixation hole at a proximal portion of the intramedullary nail 60 and at least one distal bone-anchor fixation hole at a distal portion of the intramedullary nail 60. The intramedullary nail 60 can be secured to the bone 70 by (1) drilling, for each bone-anchor fixation hole, a hole in the bone that aligns with the bone-anchor fixation hole, and (2) inserting, for each bone-anchor fixation hole, a bone anchor 40 through the bone 70 and into the bone-anchor fixation hole such that the bone anchor 40 engages the bone 70 on at least one side, such as opposed sides, of the intramedullary nail 60.

This procedure, however, can present several difficulties. For example, the proximal and distal bone-anchor fixation holes are not visible to the surgeon since the intramedullary nail 60 is disposed inside the bone 70. Moreover, as the intramedullary nail 60 is driven into the medullary canal, the intramedullary nail 60 can bend by an undetermined amount. This bending can make it difficult to predict with accuracy the location and orientation of the bone-anchor fixation holes. Therefore, a targeting system or systems can be employed to determine the location of each bone-anchor fixation hole, and/or align a cutting instrument such as a drill bit with each bone-anchor fixation hole. Once the location of a bone-anchor fixation hole is determined and/or the cutting instrument is aligned with the bone-anchor fixation hole, a hole can be drilled into the bone to the bone-anchor fixation hole. The bone anchor 40 can subsequently be inserted through the bone and into the bone-anchor fixation hole.

One method of targeting the at least one bone-anchor fixation hole includes using fluoroscopy to obtain moving X-ray images of the position of the drill bit relative to the bone-anchor fixation hole in real-time. However, the use of fluoroscopy can over expose the patient, and particularly the surgeon who performs numerous such procedures, to harmful X-rays. As an alternative to fluoroscopy, the aiming arm system 100 can be coupled to the intramedullary nail 60, and the aiming arm system 100 can be used to target at least one of the bone-anchor fixation holes with a cutting instrument such as a drill bit. Generally, the aiming arm system 100 can include an alignment aperture that aligns with at least one bone-anchor fixation hole when the aiming arm system 100 is affixed to the intramedullary nail 60. The cutting instrument can then be guided into the alignment aperture and through the bone to the bone-anchor fixation hole.

To strengthen the attachment between the bone anchor 40 and the bone 70, the bone anchor 40 can be further secured to the bone plate 30 that is positioned against the outer surface of the bone 70 and that is further secured to the bone 70 via one or more additional bone anchors. For example, the bone plate 30 can be positioned against the bone, and a first bone anchor can be inserted into an aperture in the plate 30, through the surface of the bone 70, and into the intramedullary nail 60, such that the first bone anchor attaches to the plate 30, the bone 70, and the intramedullary nail 60. Further, one or more other bone anchors can be inserted into the plate 30 adjacent the first bone anchor such that the one or more other bone anchors terminate in the bone with or without passing into the intramedullary nail 60. The one or more other bone anchors provide additional fixation to the bone that can reduce loading on the first bone anchor.

Aligning and supporting the bone plate 30 on the bone 70 while the bone plate is being secured to the bone 70 can present challenges. For example, the bone plate must be gripped and/or secured to the bone to maintain the position of the bone plate 30 relative to the intramedullary nail 60 while inserting a bone anchor 40 through an aperture in the plate 30, through the bone 70, and into an aperture in the nail 60. If a hole is pre-drilled prior to insertion to the bone anchor 40, the position of the plate 30 may also need to be maintained while a hole is drilled through the bone 70 and into the aperture in the nail 60. The guide sleeve assembly 300 is configured to secure the bone plate 30 to the bone 70 during the process of securing the bone anchor 40 to the intramedullary nail 60.

The aiming arm system 100 is configured to quickly couple to, and quickly decouple from, the insertion handle 90. The insertion handle 90 is also configured to couple to the intramedullary nail 60. The guide sleeve assembly 300 is configured to support and retain a position of the bone plate 30 against the bone 70. The aiming arm system 100 is configured to support the guide sleeve assembly 300. It will be understood, however, that the guide sleeve assembly 300, the insertion handle 90, the intramedullary nail 60, and the guide sleeve assembly 300 can be distributed separately from one another or can be distributed in groups of two or more of the aiming arm system 100, the insertion handle 90, the intramedullary nail 60, and the guide sleeve assembly 300. Therefore, examples of the present disclosure can include as few as one of the insertion handle 90, the intramedullary nail 60, and the guide sleeve assembly 300, or more than one of the aiming guide 100, the insertion handle 90, the intramedullary nail 60, and the guide sleeve assembly 300.

Referring to FIGS. 2-8, the aiming arm system 100 may include the aiming arm body 101. The aiming arm body 101 includes a coupler 102 and at least one aiming arm 104 that extends away from the coupler 102. The at least one aiming arm 104 defines at least one guide hole 106 therethrough. The coupler 102 is configured to couple the aiming arm system 100 to the insertion handle 90 such that the at least one guide hole 106 is positioned to guide an instrument, such as the guide sleeve assembly 300, towards at least one bone-anchor fixation hole of the intramedullary nail 60 when the insertion handle 90 is coupled to the intramedullary nail 60. It will be appreciated that the at least one guide hole 106 can target locations within the bone 70 external from the intramedullary nail 60 (e.g. mistarget the nail 60).

The aiming arm system 100 has an inner guide surface 108, and an outer guide surface 110 that is opposite the inner surface 108. The inner guide surface 108 can be positioned closer to the intramedullary nail 60 than the outer guide surface 110 when the aiming arm system 100 is coupled to the intramedullary nail 60. The aiming arm system 100 has a leading end 105 and a trailing end 107. The leading end 105 can be spaced from the trailing end 107 along an insertion direction I. Each guide hole 106 can extend entirely through the aiming arm body 101 from the inner guide surface 108 to the outer guide surface 110.

The at least one aiming arm 104 can include a pair of aiming arms that extend away from the coupler 104 in opposite directions. Each aiming arm 104 can extend partially around a central axis $A_L$ (see FIG. 1) that extends along the insertion direction I. For example, each aiming arm 104 can extend in a circumferential direction that extends circumferentially about the intramedullary nail 60 when the aiming arm system 100 is coupled to the intramedullary nail 60. Each aiming arm 104 can be coupled to the aiming arm body 101, or each aiming arm 104 can be formed as a single unitary piece with the aiming arm body 101. The aiming arms 104 can have any suitable configuration.

Each aiming arm 104 has at least one guide hole 106 that extends through the aiming arm 104. Each guide hole 106 extends along a central guide hole axis $A_C$ oriented along a first linear direction $L_1$. The central guide hole axis $A_C$ is aligned with one of the bone-anchor fixation holes of the intramedullary nail 60 when the aiming arm system 100 is coupled to the intramedullary nail 60 by the insertion handle 90. For example, a first guide hole 106a can extend along a first central guide hole axis $A_{C1}$ that can align with the axis $A_{B1}$ of the bone plate 30, and a second guide hole 106b can extend along a second central guide hole axis $A_{C2}$ that can align with the axis $A_{B2}$ of the bone plate 30. The alignment of the first central guide hole axis $A_{C1}$ with the axis $A_{B1}$ of the bone plate 30 can align the first guide hole 106a with the first bone-anchor opening (e.g. a target location of an anatomical implant) of the intramedullary nail 60. Similarly, the alignment of the second central guide hole axis $A_{C2}$ with the axis $A_{B2}$ of the bone plate 30 can align the second guide hole 106b with the second bone-anchor opening (e.g. another target location of an anatomical implant) of the intramedullary nail 60.

The aiming arm body 101 can include one or more additional aiming arms 112. For example, each aiming arm 104 can include an aiming arm 112 extending therefrom. In an aspect, each additional aiming arm 112 extends from a respective aiming arm 104 in the insertion direction I. Each additional aiming arm 112 can include an alignment aperture 114 extending therethrough from the inner guide surface 108 to the outer guide surface 110. Each alignment aperture 114 can align with a corresponding aperture in the bone plate 30 and/or a corresponding bone-anchor aperture in the intramedullary nail 60. Each additional aiming arm 112 can be coupled to the aiming arm 104, or each additional aiming arm 112 can be formed as a single unitary piece with the aiming arm body 101.

The first guide hole 106a and the second guide hole 106b are defined by a first guide hole surface 116a and a second guide hole surface 116b, respectively. Each guide hole surface can be configured substantially similarly and aspects described in regard to the first guide hole 106a can also apply to aspects of the second guide hole 106b. The first guide hole surface 116a can extend circumferentially about the first central guide hole axis $A_{C1}$ forming a substantially cylindrical first guide hole 106a. The first guide hole 106a extends through the aiming arm body 101 from a first opening 118a defined by the outer guide surface 110 to a second opening 120a defined by the inner guide surface 108. The first guide hole 106a is sized to receive the guide sleeve assembly 300 at least partially within.

The aiming arm body 101 further has at least one retention hole 130 that extends at least partially through the aiming arm body 104. Each retention hole 130 can extend from an opening 132 defined by an upper surface 134 of the aiming arm body 101 to a location 137 within the aiming arm body 101. The upper surface 134 extends between the inner guide surface 108 and the outer guide surface 110. Alternatively, each retention hole 130 can extend through the aiming arm body 101 from the upper surface 134 to either one of the inner guide surface 108 and the outer guide surface 110.

Each retention hole 130 extends along a central retention axis $A_R$ that is oriented along a second linear direction $L_2$. For example, a first retention hole 130a can extend along a first retention hole axis $A_{H1}$ oriented along a second linear direction $L_2$, and a second retention hole 130b can extend along a second retention hole axis $A_{H2}$ oriented along a second linear direction $L_2$. The second linear direction $L_2$ can be angularly offset from the first linear direction $L_1$. In an aspect, the second linear direction $L_2$ is substantially perpendicular to the first linear direction $L_1$.

Figure 6B:
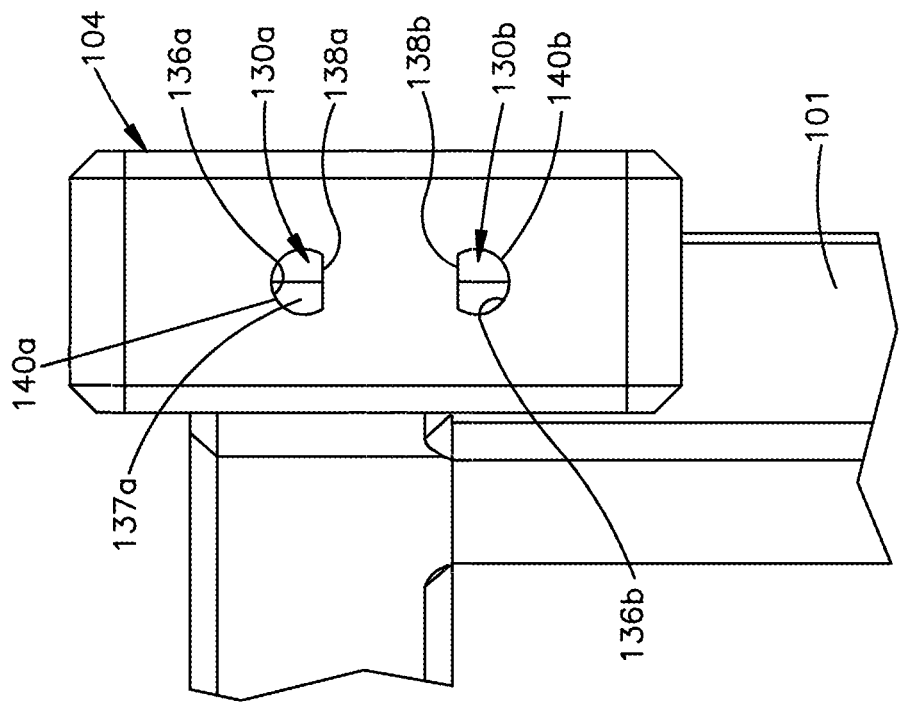
FIG. 6B illustrates a close-up top view of an alternative aspect of the aiming arm body shown FIG. 6A.
Figure 6A:
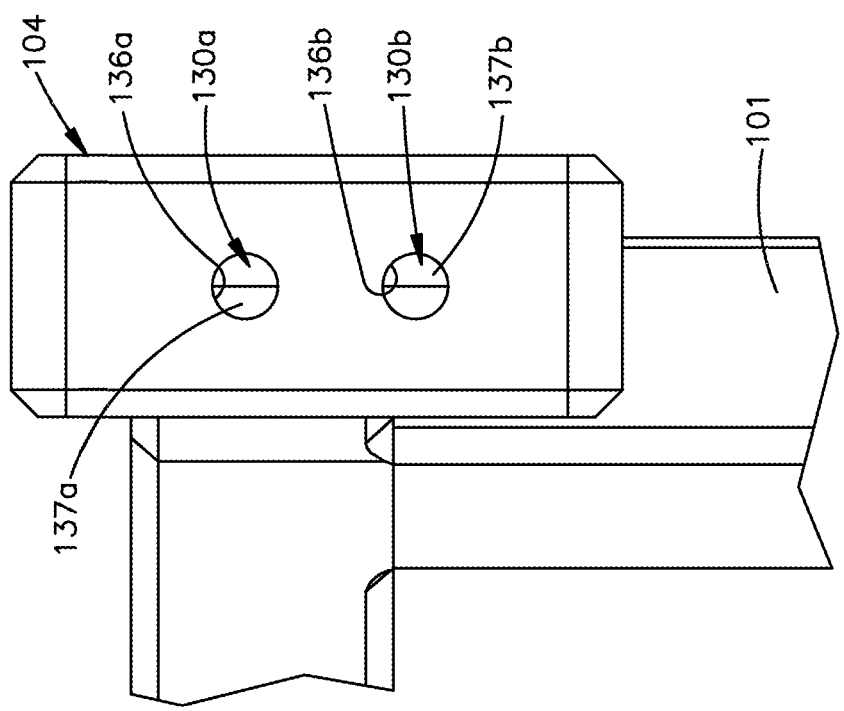
FIG. 6A illustrates a close-up top view of the aiming arm body shown in box 6 of FIG. 5.

Referring to FIGS. 4 and 6A, the first retention hole 130a and the second retention hole 130b are defined by a first retention hole surface 136a and a second retention hole surface 136b, respectively. Each retention hole surface 136a and 136b can be configured substantially similarly and aspects described in regard to the first retention hole 106a can also apply to aspects of the second retention hole 136b. The first retention hole surface 136a can extend circumferentially about the first retention hole axis $A_{H1}$ forming a substantially cylindrical first retention hole 136a. The first retention hole 136a is sized to receive a first retention element 150a at least partially within.

FIG. 6B illustrates an alternative aspect of the first and second retention holes 130a and 130b. The first retention hole surface 136a can include a flat portion 138a and a curved portion 140a. The flat portion 138a and the curved portion 140a can extend along a length of the first retention hole surface 136a from a first opening 132a to a location 137a within the aiming arm body 101. The curved portion 140a can extend at least partially about the first retention hole axis $A_{H1}$ from a first end of the flat portion 138a to a second end of the flat portion 138b. In an aspect, the curved portion 140a can form a spherical shape or partial spherical shape about the first retention hole axis $A_{H1}$ when viewed along the second linear direction $L_2$. The first retention element 150a can include an outer surface that defines a shape that corresponds to the shape of the first retention hole 130a when viewed along the second linear direction $L_2$. It will be appreciated that each retention hole 130 can include other alternative sizes and shapes configured to receive the retention element 150 within, as further described herein.

Referring to FIG. 8, each of the first and second retention holes 130a and 130b can intersect with a corresponding first and second guide hole 106a and 106b within the aiming arm body 101. For example, the first retention hole axis $A_{H1}$ of the first retention hole 130a can be positioned relative to the first central guide hole axis $A_{C1}$ of the first guide hole 106a such that a first intersection opening 142a is defined between the first retention hole surface 136a and the first guide hole surface 116a. The opening 142a can be positioned between the first opening 118a of the first guide hole 106a and the second opening 120a of the first guide hole 106a along the first linear direction $L_1$. In an aspect, the opening 142a can be positioned in a center of the first guide hole 106a along the first linear direction $L_1$. The opening 142a can also be positioned between the first opening 132a of the first retention hole surface 136a and the location 137a within the aiming arm body 101 along the second linear direction $L_2$.

Turning now to FIGS. 9-11, the aiming arm system 100 can further include the at least one retention element 150, such as the first retention element 150a and a second retention element 150b. The first retention element 150a includes a retention body 151a that has an outer retention surface 152a. Although the first retention element 150a is illustrated and described herein, it will be appreciated that a second retention element 150b or other retention elements 150 can be included in the aiming arm system 100 and configured substantially similarly as the first retention element 150a. Additionally, or alternatively, each retention element 150 can include different configurations consistent with the alternative aspects described herein.

The outer retention surface 152a extends about a central retention axis $A_{R1}$ from a first end 154 to a second end 156. The central retention axis $A_{R1}$ is oriented along the second linear direction $L_2$ when the first retention element 150a is positioned within the first retention hole 130a such that the first retention axis $A_{R1}$ is substantially parallel to the first retention hole axis $A_{H1}$ of the first retention hole 130a. The outer retention surface 152a defines a first protrusion 158 and a second protrusion 160 spaced from the first protrusion 158 in the second linear direction $L_2$. Each of the first and second protrusions 158 and 160 can extend at least partially radially outward from the first retention axis $A_{R1}$. The outer retention surface 152a further defines a recessed portion 162 that extends between the first and second protrusions 158 and 160 in the second linear direction $L_2$. The first and second protrusions 158 and 160 are spaced radially outward from the recessed portion 162 relative to the central retention axis $A_{R1}$.

The first outer retention surface 152a further includes a contact portion 164 and a curved portion 166. The contact portion 164 and the curved portion 166 can extend along a length of the first retention body 151a from the first end 154 to the second end 156. The contact portion 164 can include a substantially planar surface that extends substantially parallel to the central retention axis $A_{R1}$ from the first end 154 to the second end 156 of the retention body 101. Alternatively, the contact portion 164 can be curved or include any suitable alternatively shaped surface as desired. With reference to FIG. 11, the curved portion 166 can extend circumferentially about the central retention axis $A_{R1}$ from a first end 168 of the contact portion 164 to a second end 170 of the contact portion 164. The curved portion 166 can define a spherical shape or partial spherical shape about the first retention axis $A_{R1}$ when viewed along the second linear direction $L_2$.

Referring to FIGS. 10 and 11, the recessed portion 162 of the first outer retention surface 152a can extend substantially linearly along the second linear direction $L_2$ thereby defining a second flat portion of the first retention body 151a. The first outer retention surface 152a further includes a first neck portion 172 that extends from the recessed portion 162 at least partially radially outward to the first protrusion 158. The first outer retention surface 152a further includes a second neck portion 174 that extends from the recessed portion 162 at least partially radially outward to the second protrusion 160. The first and second neck portions 172 and 174 can include a curved configuration, a linear configuration, combinations of curved and linear portions, or another shape. The configurations of the first and second protrusions 158 and 160, the first and second neck portions 172 and 174, and the recessed portion 162 are to facilitate flexing and/or bending (e.g. a deflection) of the recessed portion 162 radially outward from the central retention axis $A_{R1}$, as further described below.

The first outer retention surface 152a of the first retention body 151a further includes a first beveled edge 176 and a second beveled edge 178. The first beveled edge 176 extends from the first end 154 toward the first protrusion 158 at least partially in the second linear direction $L_2$. The second beveled edge 178 extends from the second end 156 toward the second protrusion 160 at least partially in a direction opposing the second linear direction $L_2$. The first and/or second beveled edge 176 and 178 can facilitate insertion of the first retention element 150a into the first retention hole 130a along the first retention hole axis $A_{H1}$. In an aspect, the first retention element 150a can be substantially symmetric about a center of the first retention element 150a. The center of the first retention element 150a being between the first end 154 and the second end 156 of the first retention body 151a. The symmetry of the first retention element 150a allows either the first end 154 to be inserted through the first opening 132a of the first retention hole 130a followed by the second end 156, or the second end 156 to be inserted through the first opening 132a of the first retention hole 130a followed by the first end 154.

Figure 12:
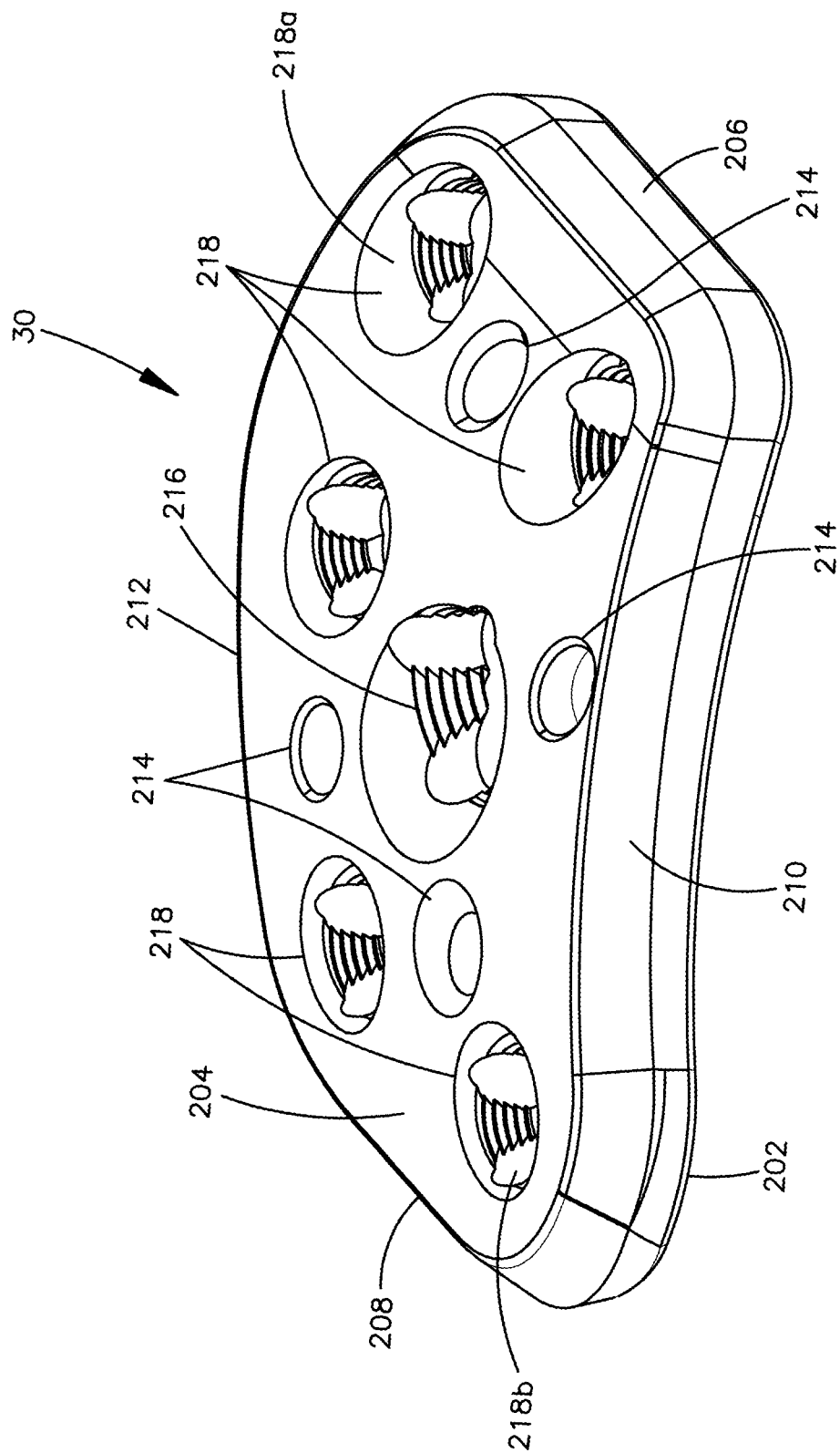
FIG. 12 illustrates a perspective view of a bone plate, according to an aspect of this disclosure.

Turning now to FIG. 12, the bone plate 30 includes a bone-facing surface 202 and an outer surface 204 opposite the bone-facing surface 202. The bone plate 30 can have a first transverse side 206 and a second transverse side 208 opposite from one another. The first and second transverse sides 206 and 208 can extend from the bone-plate facing surface 202 to the outer surface 204. The bone plate 30 can additionally or alternatively have a first lateral side 210 and a second lateral side 212 opposite from one another. The first and second lateral sides 210 and 212 can extend from the bone-plate facing surface 202 to the outer surface 204. The first and second lateral sides 210 and 212 can extend from the first transverse side 206 to the second transverse side 208. It will be understood that embodiments of the disclosure are not limited to the specific bone plate shown in FIG. 9, and that alternative bone plates are contemplated.

The bone plate 30 defines at least one bone-anchor aperture 218, such as a plurality of bone-anchor apertures 218. One or more of the bone-anchor apertures 218 are configured to extend along the axis $A_{B1}$. For example, a first bone-anchor aperture 218a can extend along the axis $A_{B1}$, and a second bone anchor aperture 218b can extend along the axis $A_{B2}$. The bone plate 30 can be positioned on the bone 70 such that each axes $A_{S1}$ and $A_{S2}$ can align with a corresponding target location (e.g. bone-anchor hole) in the intramedullary nail 60. The at least one bone-anchor aperture 218 extends through the bone plate 30 from the outer surface 204 to the bone-facing surface 202. At least one of the bone-anchor apertures 218 can be threaded to receive a threaded head of a bone anchor. Further, each bone-anchor aperture 218 can define variable-angle threading that permits a bone anchor to be inserted into the bone-anchor aperture 218 at varying angles. Alternatively, each additional bone-anchor aperture 218 can be unthreaded.

The first bone-anchor aperture 218a is spaced from the second bone-anchor aperture 218b such that the axis $A_{B1}$ of the first bone-anchor aperture 218a is offset from (i.e., not aligned with) the axis $A_{B2}$ of the second bone-anchor aperture 218b when the bone plate 30 is fastened to the intramedullary nail 60.

The bone plate 30 can also define additional bone-anchor apertures 214 and 216. The bone-anchor apertures 214 and 216 can be configured to receive a bone-plate placement tool, alignment tool, support tool, or other tool to releasable fasten the tool to the bone plate 30 to facilitate alignment and/or support of the bone plate 30 while the bone plate 30 is secured to the intramedullary nail 60. Thus, a shaft of a tool extend at least partially through the additional bone-anchor apertures 214 and 216 when the bone plate 30 is fastened to the nail 60. Further, the additional bone-anchor apertures 214 and 216 can be positioned and/or angled over a full range of angles to minimize impeding with a path of a bone anchor or drill bit. The additional bone-anchor apertures 214 and 216 can extend through the bone plate 30 from the outer surface 204 to the bone-facing surface 202. The additional bone-anchor apertures 214 and 216 can be configured to receive a bone anchor so as to further attach the bone plate 30 to the bone 70. The additional bone-anchor apertures 214 and 216 can be threaded to receive a threaded head of a bone anchor. Further, the additional bone-anchor apertures 214 and 216 can define variable-angle threading that permits a bone anchor to be inserted into the additional bone-anchor apertures 214 and 216 at varying angles. Alternatively, the bone-anchor apertures 214 and 216 can be unthreaded.

Figure 13:
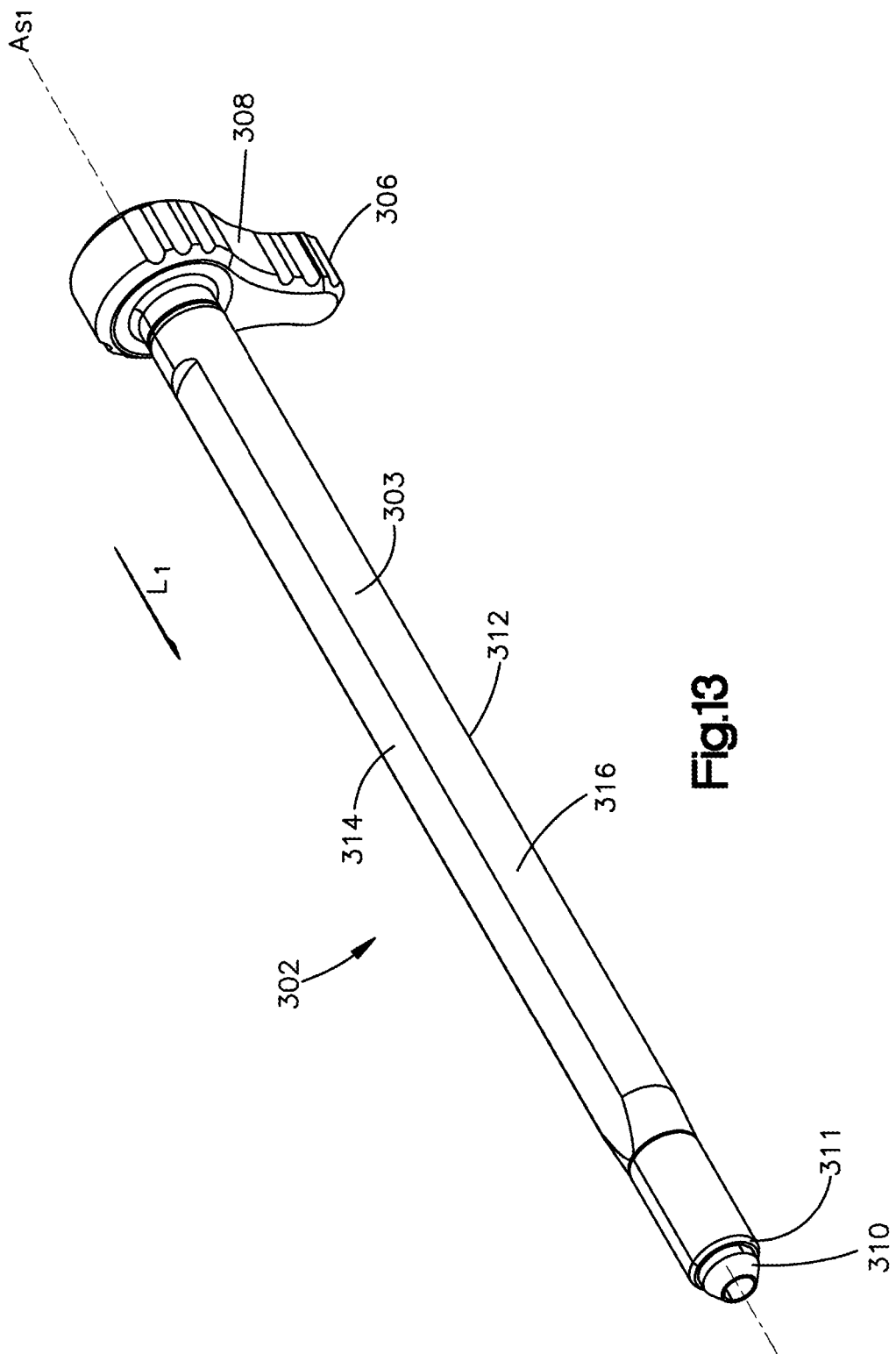
FIG. 13 illustrates a perspective view of a guide sleeve assembly, according to an aspect of this disclosure.
Figure 18:
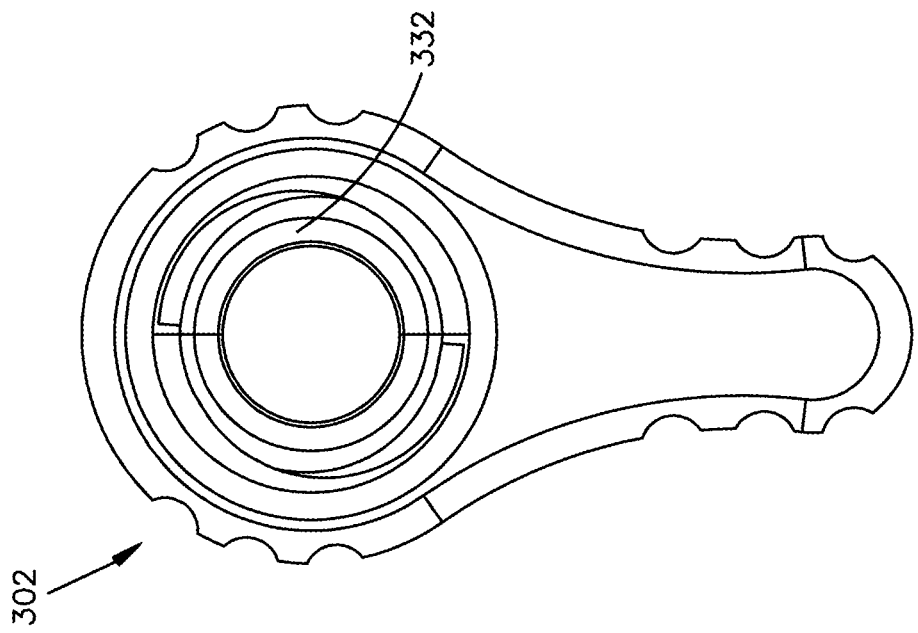
FIG. 18 illustrates a rear view of the outer guide sleeve shown in FIG. 14.
Figure 17:
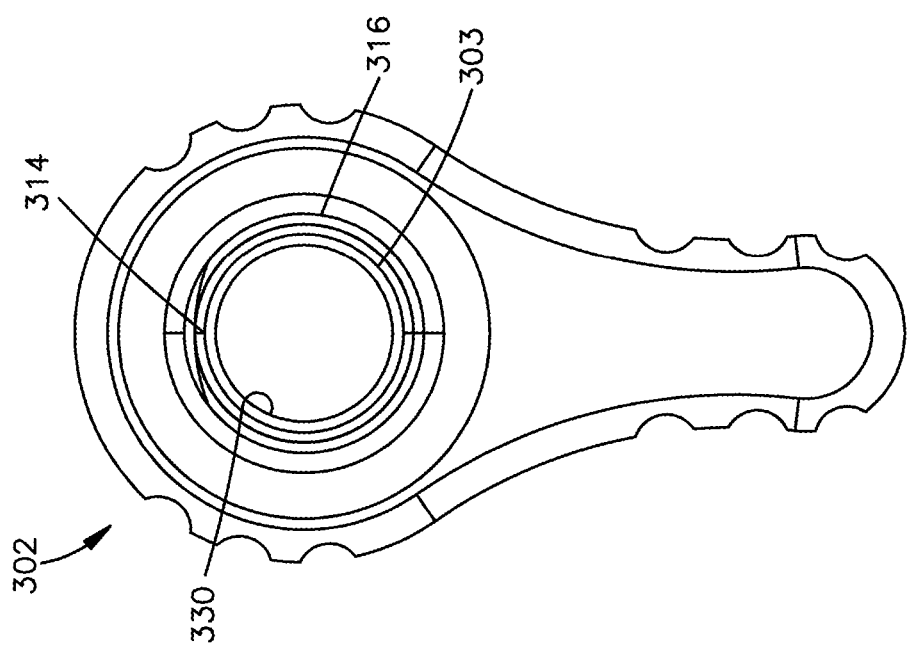
FIG. 17 illustrates a front view of the outer guide sleeve shown in FIG. 14.
Figure 23:
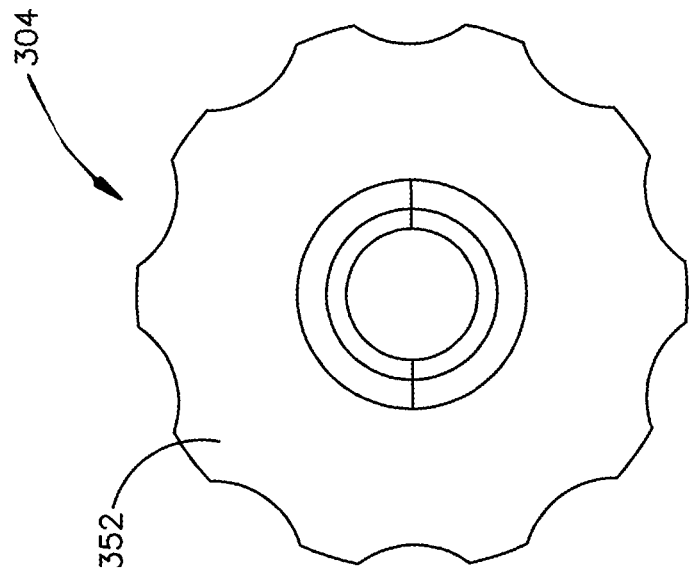
FIG. 23 illustrates a rear view of the outer guide sleeve shown in FIG. 19.
Figure 22:
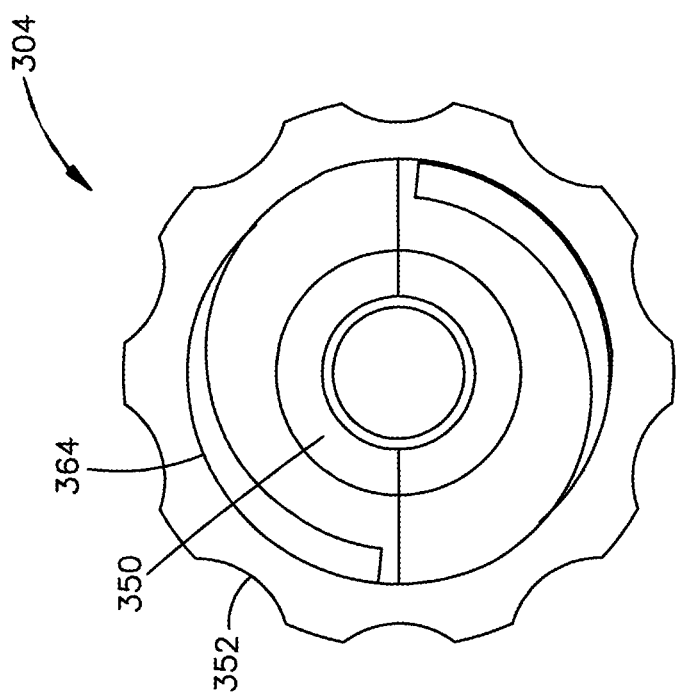
FIG. 22 illustrates a front view of the inner guide sleeve shown in FIG. 19.

Turning now to FIG. 13, the guide sleeve assembly 300 includes an outer guide sleeve 302 and an inner guide sleeve 304. The inner guide sleeve 304 is insertable through the outer guide sleeve 302. The inner guide sleeve 304 can be coupled to the outer guide sleeve 302 to substantially prevent movement between the inner and outer guide sleeves 302 and 304. The guide sleeve assembly 300 is configured to be inserted through the at least one guide hole 106 of the aiming arm system 100 to align with the bone plate 30 and the intramedullary nail 60. The alignment of the guide sleeve assembly 300 with the bone plate 30 and the intramedullary nail 60 enables a bone anchor and/or a drill be to be inserted through the guide sleeve assembly 300 and into and/or through the bone plate 30, the bone 70, and the nail 60.

Referring to FIGS. 14-18, the outer guide sleeve 302 includes an outer guide body 303 and an outer sleeve handle 306. The outer sleeve handle 306 is configured to be gripped and/or controlled by a surgeon during a medical procedure to align the outer guide sleeve 302 relative to the inner guide sleeve 304 and/or align the outer guide sleeve 302 relative to the aiming arm system 100. The outer guide body 303 extends along a central outer guide sleeve axis $A_{S1}$, that can align with the first central guide hole axis $A_{C1}$ of the first guide hole 106a when the guide sleeve assembly 300 is inserted into the first guide hole 106a. It will be appreciated that the central outer guide sleeve axis $A_{S1}$ can align with other central guide hole axes $A_C$ of guide holes 106 defined by the aiming arm 104. For example, the central outer guide sleeve axis $A_{S1}$ can align with the second central guide hole axis $A_{C2}$ of the second guide hole 106b when the guide sleeve assembly 300 is inserted into the second guide hole 106b. The outer guide sleeve 302 is configured and sized to be inserted into and extend through a corresponding guide hole 106 in the first linear direction $L_1$, thereby orienting the central outer guide sleeve axis $A_{S1}$ along the first linear direction $L_1$.

The outer sleeve handle 306 extends along the central outer guide sleeve axis $A_{S1}$ from the outer sleeve body 303 to a first end 308 of the outer sleeve guide 302. The outer guide body 303 extends along the central outer guide sleeve axis $A_{S1}$ from the outer sleeve handle 306 to a second end 310. The outer guide body 303 includes an outer sleeve surface 312 that extends about the central outer guide sleeve axis $A_{S1}$ between the outer sleeve handle 306 and the second end 310. The outer sleeve surface 312 comprises a reduced cross-sectional dimension portion 314 and a curved portion 316. The curved portion 316 extends about the central outer guide sleeve axis $A_{S1}$ from a first end 318 of the reduced portion 314 to a second end 320 of the reduced portion 314. The curved portion 316 can extend along a length of the outer sleeve surface 312 from the handle 306 to the second end 310. Alternatively, the curved portion 316 can extend along a part of the outer sleeve surface 312 between the handle 306 and the second end 310. For example, the curved portion 316 could extend from the second end 310 to a location on the outer sleeve surface 312 between the handle 306 and the second end 310.

The curved portion 316 is spaced from the central outer guide sleeve axis $A_{S1}$ by a first dimension $R_1$. The first dimension $R_1$ extends substantially perpendicular to the central outer guide sleeve axis $A_{S1}$. The curved portion 316 can have a substantially constant first dimension $R_1$ along the length of the outer sleeve surface 312 from the handle 306 to the second end 310. Alternatively, the curved portion 316 can vary in size and or dimension along the length of the outer sleeve surface 312. For example, the curved portion 316 can have a first dimension $R_1$ along a length of the outer sleeve surface 312 between the handle 306 and a location 315 between the handle 306 and the second end 310, and the curved portion 316 can have a first dimension $R'_1$ between the location and the second end 310, whereby the first dimension $R'_1$ is less than the first dimension $R_1$. The reduced first dimension $R'_1$ can facilitate insertion of the outer sleeve guide 302 into the corresponding guide hole 106. Additionally, the second end 310 of the outer sleeve guide 302 can include a beveled edge to further facilitate insertion of the outer sleeve guide 302.

The reduced portion 314 can extend along a length of the outer sleeve surface 312 from the handle 306 to the second end 310. Alternatively, the reduced portion 314 can extend along a part of the outer sleeve surface 312 between the handle 306 and the second end 310. For example, the reduced portion 314 can extend from a first location 326 on the outer sleeve surface 312 positioned between the handle 306 and the second end 310 to a second location 328 on the outer surface 312 positioned between the handle 306 and the second end 310.

The reduced portion 314 is spaced from the central outer guide sleeve axis $A_{S1}$ by a second dimension $R_2$. The second dimension $R_2$ extends substantially perpendicular to the central outer guide sleeve axis $A_{S1}$. The second dimension $R_2$ of the reduced portion 314 can vary along a width of the reduced portion 314 between the first end 318 and the second end 320 of the reduced portion 314. For example, the second dimension $R_2$ at the first end 318 and the second end 320 can be greater than the second dimension $R_2$ between the first and second ends 318 and 320 of the reduced portion 314. The second dimension $R_2$ of the reduced portion 314 is less than the first dimension $R_1$ of the curved portion 316 that extends from the first end 318 to the second end 320 of the reduced portion 314. The size of the second dimension $R_2$ of the reduced portion 314 relative to the size of the first dimension $R_1$ of the curved portion 316 enables movement of the guide sleeve assembly 300 within the guide hole 106 when the aiming arm system 100 is in an unlocked configuration, as further described below.

In an aspect, the reduced portion 314 can define a substantially flat planar surface. In an alternative aspect, the reduced portion 314 can be curved or partially curved about the central outer guide sleeve axis $A_{S1}$ from the first end 318 to the second end 320 of the reduced portion 314. For example, the reduced portion 314 can have a substantially constant second dimension $R_2$ along a circumferential width of the outer sleeve surface 312 from first end 318 to the second 320 of the reduced portion 314, and along a length of the outer sleeve surface 312 from the first location 326 to the second location 328 on the outer sleeve surface 312.

The outer guide sleeve 302 further includes an inner guide surface 330 that defines an outer guide aperture 331 that extends through the outer guide sleeve 302 about the central outer guide sleeve axis $A_{S1}$ from the first end 308 to the second end 310 of the outer guide sleeve 302. The inner guide surface 330 includes a first coupler 332. The first coupler 332 can include a threaded portion, a snap-fit element, a recess, a protrusion, or other coupling element configured to couple the outer guide sleeve 302 to the inner guide sleeve 304 when the inner guide sleeve 304 is inserted and positioned within the outer guide aperture 331. The first coupler 332 can be positioned along the inner guide surface 330 between the first and second ends 308 and 310 of the outer guide sleeve 302. In an aspect, the first coupler 332 is positioned on a portion the inner guide surface 330 within the handle 306.

Referring to FIGS. 19-23, the inner guide sleeve 304 includes an inner guide body 350 and an inner sleeve handle 352. The inner sleeve handle 352 is configured to be gripped and/or controlled by a surgeon before or during a medical procedure to align the inner guide sleeve 304 relative to the outer guide sleeve 302 and/or align and couple the inner guide sleeve 304 to the bone plate 30. The inner guide body 350 extends along a central inner guide sleeve axis $A_{S2}$, that can align with the central guide hole axis $A_C$ of the guide hole 106 when the guide sleeve assembly 300 is inserted into the guide hole 106. The inner guide sleeve 302 is configured and sized to be inserted into and extend through the outer guide aperture 331 of the outer guide sleeve 302 in the first linear direction $L_1$, thereby orienting the central inner guide sleeve axis $A_{S2}$ along the first linear direction $L_1$.

The inner sleeve handle 352 extends along the central inner guide sleeve axis $A_{S2}$ from the inner guide body 350 to a first end 358 (e.g. a proximal end) of the inner sleeve guide 304. The inner guide body 350 extends along the central inner guide sleeve axis $A_{S2}$ from the inner sleeve handle 352 to a second end 360 (e.g. a distal end) of the inner sleeve guide 304. The inner guide body 350 includes an outer sleeve surface 362 that extends about the central inner guide sleeve axis $A_{S2}$ between the inner sleeve handle 352 and the second end 360 of the inner sleeve guide 304. The outer sleeve surface 362 of the inner sleeve guide 304 includes a second coupler 364. The second coupler 364 can include a threaded portion, a snap-fit element, a recess, a protrusion, or other coupling element configured to couple to the first coupler 332 of the outer guide sleeve 302 when the inner guide sleeve 304 is inserted and positioned within the outer guide aperture 331. The second coupler 364 is configured to couple to the first coupler 332 such that the inner guide sleeve 304 is substantially prevented from moving along the first linear direction $L_1$ within the outer guide aperture 331 of the outer guide sleeve 302.

The second coupler 364 can be positioned along the outer guide surface 364 of the inner guide sleeve 304 between the first and second ends 358 and 360 of the inner guide sleeve 304. The position of the second coupler 364 can correspond to a position of the first coupler 332 on the inner guide surface 330. For example, the second coupler 364 can be positioned relative to the first coupler 332 such that when the first and second couplers 332 and 364 are coupled to one another (e.g. a coupled position), the inner guide sleeve 304 extends through an opening 311 defined by the second end 310 of the outer guide sleeve 302, and the second end 360 of the inner guide sleeve 304 is located exterior to the outer guide sleeve 302. When the first and second couplers 332 are de-coupled (e.g. a de-coupled position), the inner guide sleeve 304 can be retracted in a direction opposite to the first linear direction $L_1$ within the outer guide sleeve 302. In an aspect, when the inner guide sleeve 304 and the outer guide sleeve 302 are in the de-coupled position, the second end 360 of the inner guide sleeve 304 can be positioned within the guide aperture 331 of the outer guide sleeve 302

The inner guide sleeve 304 further includes an inner guide surface 370 that defines an inner guide aperture 371 that extends through the inner guide sleeve 304 about the central inner guide sleeve axis $A_{S2}$ from the first end 358 to the second end 360 of the inner guide sleeve 304. The inner guide aperture 371 of the inner guide sleeve 304 can have a substantially cylindrical shape such that a cross-sectional dimension (e.g. a diameter) of the inner guide aperture 371 is substantially the same along the length of the inner guide sleeve 304 from the first end 358 to the second end 360. Alternatively, the inner guide aperture 371 can include other shapes, for example, a conical shape, a reduced diameter portion, combinations thereof, or another shape or shapes to facilitate alignment and positioning of a bone anchor and/or a drill bit along the plate axis $A_B$ of the bone plate 30.

The outer guide surface 362 of the inner guide sleeve 304 further defines a beveled edge 374. The beveled edge 374 extends from the second end 360 of the inner guide sleeve 304 toward the first end 358 of the inner guide sleeve 304. The beveled edge 274 having a minimum cross-sectional dimension (e.g. a diameter) at the second end 358, and a maximum diameter spaced from the second end 358 toward the first end 358. The beveled edge 358 is configured to be positioned at least partially within the bone-anchor aperture 218 of the bone plate 30 to provide a temporary connection between the bone plate 30 and the guide sleeve assembly 300 to support the plate 30 while a hole is drilled into the bone 70 and/or a bone anchor is being positioned within one or more bone-anchor apertures of the bone plate 30. In an aspect, the beveled edge 374 can correspond to a beveled edge of the bone-anchor aperture 218 to enhance the connection between the guide sleeve assembly 300 and the plate 30.

Figure 24:
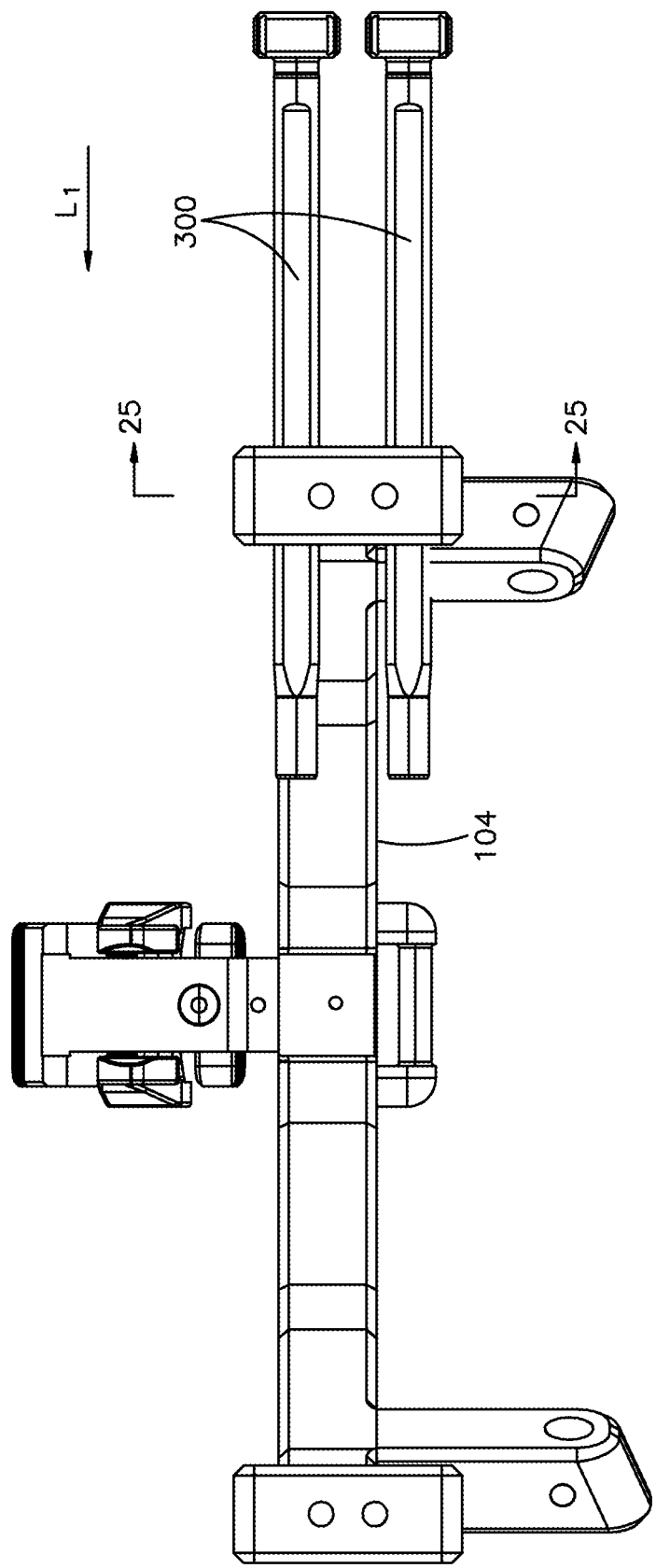
FIG. 24 illustrates a top view of the aiming arm body shown in FIG. 2 with the retention element shown in FIG. 9 and the guide sleeve assembly shown in FIG. 13 both positioned within the aiming arm body, according to an aspect of this disclosure.
Figure 25A:
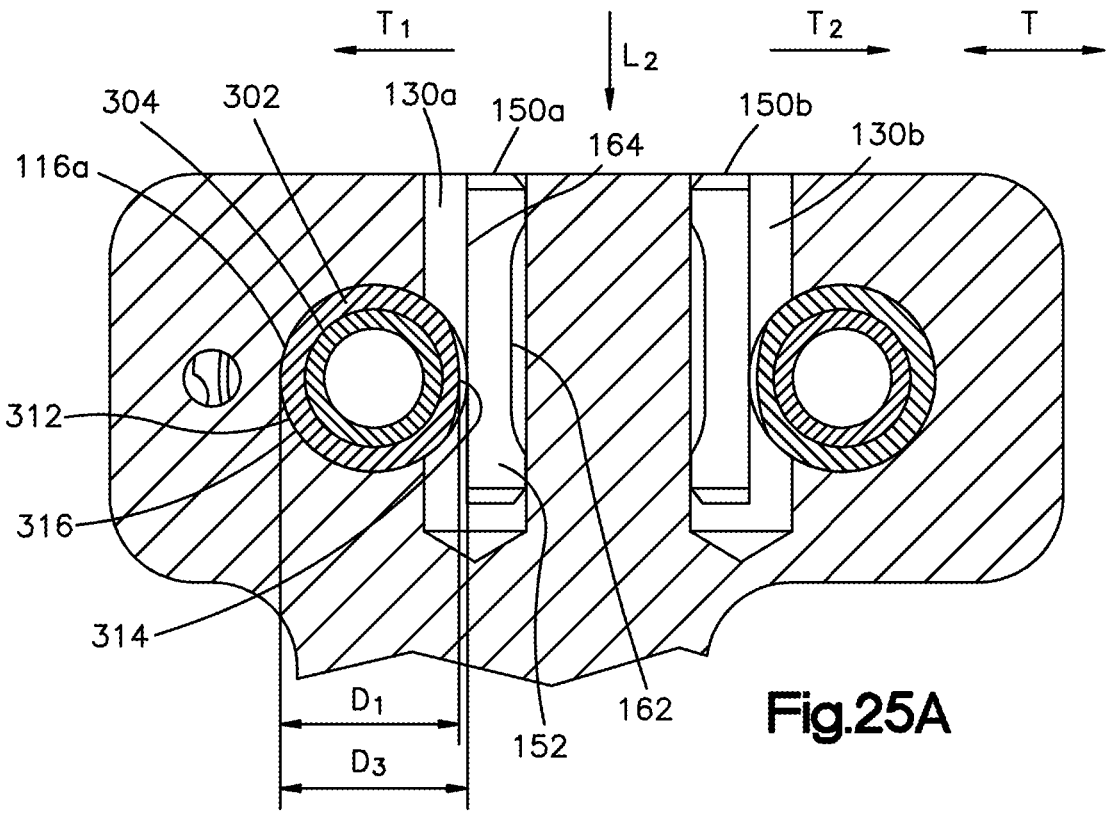
FIG. 25A illustrates a cross-sectional view of the aiming arm body, the retention element, and the guide sleeve assembly taken along line 25-25 shown in FIG. 24 in an unlocked configuration.
Figure 25B:
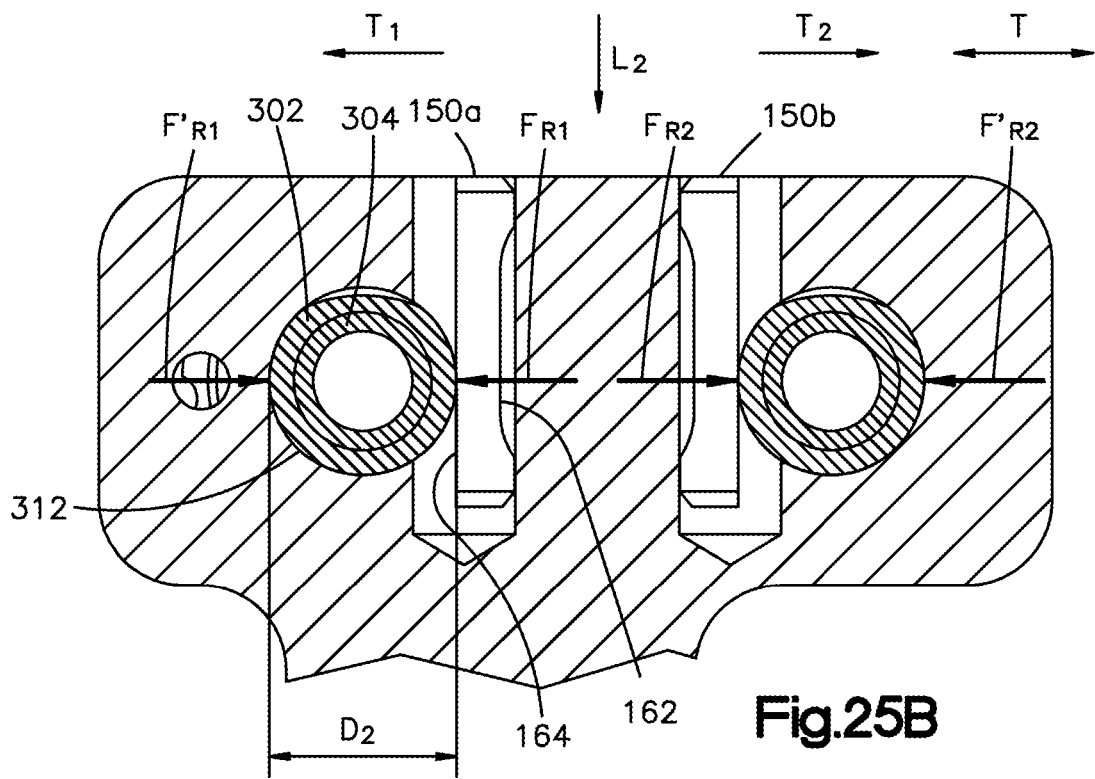
FIG. 25B illustrates a cross-sectional view of the aiming arm body, the retention element, and the guide sleeve assembly taken along line 25-25 shown in FIG. 24 in an locked configuration.

Turning now to FIGS. 24, 25A, and 25B, the guide sleeve assembly 300 is positioned within the first guide hole 106a and another guide sleeve assembly 300 is positioned within the second guide aperture 106b. The guide sleeve assembly 300 is inserted within the guide hole 106 in the first linear direction $L_1$, such that the central outer guide sleeve axis $A_{S1}$ of the outer guide sleeve 302 and central inner guide sleeve axis $A_{S2}$ of the inner guide sleeve 304 are substantially parallel to the central guide hole axis $A_C$.

The first and second retention elements 150a and 150b can be inserted into the retention holes 130a and 130b in the second linear direction $L_2$ such that the first and second retention axes $A_{R1}$ and $A_{R2}$ are substantially parallel to the first and second first retention hole axes $A_{H1}$ and $A_{H2}$, respectively. The first and second retention elements 150a and 150b can be inserted into the respective retention holes 130a and 130b either before or after the guide sleeve assembly 300 is inserted into the guide hole 106.

After the retention element 150 has been inserted into respective retention holes 130, the aiming arm system 100 can be transitioned between an unlocked configuration whereby the guide sleeve assembly 300 is insertable through the guide hole 106 along the first linear direction $L_1$, and a locked configuration whereby the retention element 150 applies a retention force FR to the outer guide sleeve 304 that substantially prevents the guide sleeve from moving further along the first linear direction $L_1$. The outer guide sleeve 304 is configured to rotate within the guide hole 106 about the central guide hole axis $A_C$ between an unlocked position (e.g. FIG. 25A) in which the aiming arm system 100 is in the unlocked configuration, and a locked position (e.g. FIG. 25B) in which the aiming arm system 100 is in the locked configuration. In an aspect, the retention element 150 is configured to rotate about the retention hole axis $A_H$ relative to the outer guide sleeve 304 between an unlocked position and a locked position.

In the unlocked position of the outer guide sleeve 304, a surgeon can move the guide sleeve assembly 300 to a desired location, such as adjacent to the bone-anchor aperture 218 of the bone plate 30, and lock the guide sleeve assembly 300 in position by rotating the outer guide sleeve 304.

In a first rotational position of the guide sleeve 302, the outer sleeve surface 312 defines a first outer dimension $D_1$ that extends through the central guide sleeve axis $A_{S1}$ in a first transverse direction $T_1$. Of a transverse direction T that includes the first transverse direction T1 and a second transverse direction $T_2$ that is opposite the first transverse direction T1. The transverse direction T, and thus each of the first transverse direction T1 and the second transverse direction T2, is oriented perpendicular to each of the first and second linear directions $L_1$ and $L_2$. The first outer dimension $D_1$ can be defined by first and second points of the outer sleeve surface 312 that are opposite each other and aligned with each other along the transverse direction T. In particular, the first outer dimension $D_1$ extends from the first point to the second point along the transverse direction T. Further, the first and second points are aligned with the respective first or second retention element 150a or 150b along the transverse direction T. It should be appreciated that the first and second points can be selected at any select location along the length of the outer guide sleeve in the first linear direction $L_1$ (see FIG. 13) that is aligned with the respective retention element along the transverse direction T. In the first rotational position, the contact portion 164 of the retention element 150 faces the reduced portion 314 of the outer sleeve surface 312 in the first transverse direction $T_1$. Further, one of the first and second points is located on the reduced portion 314, and the other of the first and second points is located on the curved portion 316.

The retention element 150 defines a third dimension $D_3$ that extends from a first point on a surface of the contact portion 164 of the retention element 150 to a second point on the inner guide surface 116 of the guide hole 106 that is opposite the contact portion 164 along the transverse direction T. The third dimension $D_3$ is greater than the first dimension $D_1$ when the guide sleeve 302 is in the first rotational position, thereby spacing the retention element 150 from the outer guide sleeve 302 along the transverse direction T. Because the third dimension $D_3$ is greater than the first dimension $D_1$, the retention element 150 and the guide sleeve 302 are movable with respect to each other along the first linear dimension $L_1$ (see FIG. 13). Otherwise stated, the retention element does not interfere with movement of the guide sleeve 302 relative to the retention element 150, and thus relative to the aiming guide 104, along the first linear dimension $L_1$. Thus, the first rotational position of the guide sleeve can be referred to as an unlocked position of the outer guide sleeve 302.

The guide sleeve 302 can be rotated about its central outer guide sleeve axis $A_{S1}$ from the first rotational position to a second rotational position. As will be appreciated from the description below, the second rotational position of the guide sleeve 302 can be referred to as a locked position. In the second rotational position of the guide sleeve 302, the outer sleeve surface 312 defines a second dimension $D_2$ that extends through the central guide sleeve axis $A_{S1}$ along the transverse direction T. The second dimension $D_2$ can be defined by third and fourth points on opposed sides of the outer sleeve surface 312 that are opposite each other and aligned with each other along the transverse direction T. In particular, the second dimension $D_2$ extends from the third point to the fourth point along the transverse direction T. Further, the third and fourth points can be disposed at the select location along the length of the guide sleeve 302 that is aligned with the retention element 150 along the transverse direction T. The second dimension $D_2$ is greater than the first dimension $D_1$. Accordingly, the outer sleeve surface 312 of the outer guide sleeve 302 to contact the retention element 150 in the locked position. In particular, the outer sleeve surface 312 contacts the surface of the contact portion 164 of the retention element 150. The outer sleeve surface 312 can thus urge the contact portion 164 of the retention element 150 to compress along the transverse direction T when the guide sleeve 302 is rotated from the first rotational position to the second rotational position. For instance, recessed portion 162 of the retention element 150 defines a region of reduced thickness of the retention element 150 that allows the retention element 150 to flex in the transverse direction away from the guide sleeve 302. Alternatively or additionally, a compressible material can define the outer surface of the guide sleeve 302 that compresses along the transverse direction T when the guide sleeve 302 is rotated from the first rotational position to the second rotational position. The retention element 150 can be positioned within the retention hole 130 such that the outer sleeve surface 312 contacts the contact portion 164 of the outer retention surface 152 of the retention element 150. The contact portion 164 can be disposed opposite the recessed portion 162 along the transverse direction T. The recessed portion 162 can deflect away from (e.g. radially outward) the central guide hole axis $A_C$ of the guide hole 106, thereby allowing the contact portion 164 of the retention element 150 to compresses in the manner described above. In the locked position of the outer guide sleeve 302, the recessed portion 162 of the retention element 150 can be positioned a greater distance away from the central guide hole axis $A_C$ than a distance that the retention element 150 is positioned away from the central guide hole axis Ac.

In the locked position, the third dimension $D_3$ defined by the retention element 150 is naturally less than the second dimension $D_2$, causing the retention element 150 to contact and provide the retention force $F'_{R1}$ to the outer guide sleeve 302 in the first transverse direction $T_1$. It will be appreciated that an opposing retention force $F'_{R1}$ can also be applied by the inner guide surface 116 of the guide hole 106 in a second transverse direction $T_2$ to the outer guide sleeve 302. The second transverse direction $T_2$ is oriented perpendicular to each of the first and second linear directions $L_1$ and $L_2$. Further, the second transverse direction $T_2$ is opposite the first transverse direction $T_1$. The contact between the retention element 150 and the outer guide sleeve 302 can form an interference fit connection, whereby the retention force FRI comprises a friction force applied to the outer guide sleeve 302 by the retention element 150 in a direction opposing a direction of movement of the outer guide sleeve 302 within the guide hole 106.

In an alternative example, the retention element 150 can be configured to rotate within the retention hole 130 between an unlocked position in which the aiming arm system 100 is in the unlocked configuration, and a locked position in which the aiming arm system 100 is in the locked configuration. For example, the outer sleeve surface 312 of the outer guide sleeve 302 can be substantially cylindrical along a length of the outer guide body 303. The retention element can be transitioned between an unlocked position and a locked position. In the unlocked position, the retention element 150 is spaced from the outer sleeve surface 312. In the locked position, the retention element 150 contacts the outer sleeve surface 312 of the outer guide body 302, whereby the contact on the outer retention surface 152 of the retention element 150 is at a location on the outer retention surface 152 that opposes the recessed portion 162. The contact between the outer retention surface 152 and the outer sleeve surface 312 deflects the recessed portion 162 away from the outer sleeve surface 312 as the retention element 150 provides the retention force $F_{R1}$ to the outer sleeve guide 302.

The retention element 150 can be positioned externally from the aiming arm body 101. For example, the retention element 150 can be separate from the aiming arm bod 101 and coupled to the aiming arm body 101. For instance, the retention element 150 can be coupled to the inner guide surface 108 or the outer guide surface 110, or other surface of the aiming arm body 101. The retention element 150 can be coupled to a surface of the aiming arm body 101 such that the third dimension $D_3$ is defined between two surfaces of the retention element 150. The two surfaces can oppose each other in the first transverse direction $T_1$, and can compose a portion of the guide hole 106. The third dimension $D_3$ defined between the two surfaces of the retention element 150 is less than the first dimension $D_1$ defined by the two points on opposing sides of the outer sleeve surface 312, causing the retention element 150 to contact and provide the retention force $F_{R1}$ to the outer guide sleeve 302 in the first transverse direction $T_1$, and also provide the opposing retention force FRI to the outer guide sleeve 302 in the second transverse direction $T_2$, when the outer guide sleeve 302 is rotated to the locked position. Alternatively, the retention element 150 can be monolithic with the aiming arm bod 101.

During use of the system 10, after the central guide hole axis $A_C$ has been aligned with the target location of the intramedullary nail 60 and the aiming arm system 100 has been transitioned to locked configuration, posterior bone-anchor screws and/or a drill bit can be inserted through the inner guide aperture 371 of the inner guide sleeve 304 and through the bone plate 30, the bone 70 and/or the intramedullary nail 60. After the bone-anchors have been inserted, the aiming arm system 100 can be transitioned to the unlocked configuration and the guide sleeve assembly 300 can be removed from the guide hole 106.

Although the disclosure has been described in detail, it should be understood that various changes, substitutions, and alterations can be made herein without departing from the spirit and scope of the invention as defined by the appended claims. Additionally, any of the embodiments disclosed herein can incorporate features disclosed with respect to any of the other embodiments disclosed herein. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. An aiming arm system, comprising:
an aiming arm having 1) an aiming arm body and a guide hole that extends through the aiming arm body along a central guide hole axis, wherein the aiming arm is configured to be positioned such that the central guide hole axis is aligned with a target location of an anatomical implant, and 2) a retention element supported relative to the aiming arm body; and
a guide sleeve that extends along a linear central guide sleeve axis, the guide sleeve sized to be inserted into the guide hole, wherein relative rotation between the guide sleeve and the retention element transitions the aiming arm system between an unlocked configuration whereby the guide sleeve is movable in the guide hole along the central guide hole axis, and a locked configuration whereby the retention element applies a retention force to the guide sleeve that resists movement of the guide sleeve along the central guide hole axis, wherein the guide sleeve is an outer guide sleeve, and has an inner guide surface that defines an outer guide aperture that extends through the outer guide sleeve along the central guide sleeve axis, wherein the inner guide surface includes a first coupler, the system further comprising:
an inner guide sleeve that extends along a central inner guide sleeve axis, the inner guide sleeve sized to be inserted into the outer guide aperture, the inner guide sleeve having an outer guide surface that includes a second coupler,
wherein the first and second couplers are configured to couple to one another such that the inner guide sleeve is substantially prevented from moving within the outer guide aperture.

2. The system of claim 1, wherein the inner guide sleeve is configured to move between a de-coupled position in which the first and second couplers are de-coupled from each other and a distal end of the inner guide sleeve is positioned within the outer guide aperture of the outer guide sleeve, and a coupled position in which the first and second couplers are coupled to one another and a portion of the inner guide sleeve extends through a distal opening defined by a distal end of the outer guide sleeve such that the distal end of the inner guide sleeve is located exterior to the outer guide sleeve.

3. The system of claim 1, wherein the retention element extends along a central retention axis, wherein the aiming arm further has a retention hole that extends at least partially through the aiming arm body along a central retention hole axis, wherein the retention element is sized to be inserted through the retention hole, wherein the retention element comprises a retention body having an outer retention surface that extends about the central retention axis, the outer retention surface defining a first protrusion and a second protrusion spaced from the first protrusion, the outer retention surface further defining a recessed portion that extends between the first and second protrusions,
wherein in the unlocked configuration of the aiming arm system, the recessed portion is located a first radial distance from the central guide hole axis of the alignment guide hole, and wherein in the locked position of the outer guide sleeve, the recessed portion is located a second radial distance from the central guide hole axis that is greater than the first radial distance.

\* \* \* \* \*